US012629427B2

(12) United States Patent
De La Fuente Freire et al.

(10) Patent No.: US 12,629,427 B2
(45) Date of Patent: May 19, 2026

(54) NANOSYSTEMS AS SELECTIVE VEHICLES

(71) Applicants: FUNDACIÓN INSTITUTO DE INVESTIGACIÓN SANITARIA DE SANTIAGO DE COMPOSTELA (FIDIS), Santiago de Compostela (ES); SERVIZO GALEGO DE SAÚDE, Santiago de Compostela (ES)

(72) Inventors: María De La Fuente Freire, Santiago de Compostela (ES); Rafael López López, Santiago de Compostela (ES); Belén López Bouzo, Santiago de Compostela (ES); Abi Judit Vázquez Ríos, Santiago de Compostela (ES); Marta Alonso Nocelo, Santiago de Compostela (ES)

(73) Assignee: SERVIZO GALEGO DE SAÚDE FUNDACIÓN INSTITUTO DE INVESTIGACIÓN SANITARIA DE SANTIAGO DE COMPOSTELA (FIDIS)

( * ) Notice: Subject to any disclaimer, the term of this patent is extended or adjusted under 35 U.S.C. 154(b) by 0 days.

(21) Appl. No.: 18/054,065

(22) Filed: Nov. 9, 2022

(65) Prior Publication Data

US 2023/0190953 A1 Jun. 22, 2023

Related U.S. Application Data

(63) Continuation of application No. 16/962,196, filed as application No. PCT/EP2019/050979 on Jan. 15, 2019, now abandoned.

(30) Foreign Application Priority Data

Jan. 15, 2018 (EP) .................................... 18382012

(51) Int. Cl.

| | |
|---|---|
| *A61K 47/69* | (2017.01) |
| *A61K 9/107* | (2006.01) |
| *A61K 31/05* | (2006.01) |
| *A61K 31/12* | (2006.01) |
| *A61K 31/337* | (2006.01) |
| *A61K 31/513* | (2006.01) |
| *A61K 31/685* | (2006.01) |
| *A61K 31/7048* | (2006.01) |
| *A61K 31/7068* | (2006.01) |
| *A61K 41/00* | (2020.01) |
| *A61K 45/06* | (2006.01) |
| *A61K 47/10* | (2017.01) |
| *A61K 47/22* | (2006.01) |
| *A61K 47/24* | (2006.01) |
| *A61K 47/54* | (2017.01) |
| *A61K 47/64* | (2017.01) |

(Continued)

(52) U.S. Cl.
CPC ........ *A61K 47/6907* (2017.08); *A61K 9/1075* (2013.01); *A61K 31/05* (2013.01); *A61K 31/12* (2013.01); *A61K 31/337* (2013.01); *A61K 31/513* (2013.01); *A61K 31/685* (2013.01); *A61K 31/7048* (2013.01); *A61K 31/7068* (2013.01); *A61K 41/0071* (2013.01); *A61K 45/06* (2013.01); *A61K 47/10* (2013.01); *A61K 47/22* (2013.01); *A61K 47/24* (2013.01); *A61K 47/549* (2017.08); *A61K 47/64* (2017.08); *A61K 47/6425* (2017.08); *A61K 49/0002* (2013.01); *A61K 49/0078* (2013.01); *A61K 51/122* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 9,072,775 | B2 * | 7/2015 | Goutayer ............... | C09K 23/14 |
| 2007/0148194 | A1 * | 6/2007 | Amiji .................. | A61K 9/0095 424/400 |

FOREIGN PATENT DOCUMENTS

| | | | |
|---|---|---|---|
| RU | 2535022 | C2 | 12/2014 |
| WO | WO 2015013566 | A1 | 1/2015 |

OTHER PUBLICATIONS

Kumar R, Mehta SK. Formulation and physiochemical study of α-tocopherol based oil in water nanoemulsion stabilized with non toxic, biodegradable surfactant: Sodium stearoyl lactate. Ultrasonics sonochemistry. Sep. 1, 2017;38:570-8. (Year: 2017).*

(Continued)

*Primary Examiner* — Nissa M Westerberg
(74) *Attorney, Agent, or Firm* — Seed Intellectual Property Law Group LLP

(57) ABSTRACT

Various oil-in-water (O/W) nanoemulsions containing an oil phase or oil core, preferably selected from vitamin E or oleic acid, stabilized by a sphingolipid of the sphingomyelin type, and optionally other lipids such as phospholipids, cholesterol, octadecylamine, DOTAP (N-[1-(2,3-Dioleoyloxy) propyl]-N,N,N-trimethylammonium methyl-sulfate), and PEGylated derivatives (derivatives with polyethylene glycol), for use as a nanotech vehicle, for example for the management of cancer and metastatic disease. Said nanoemulsions can be functionalized with ligands capable of interacting or binding to receptors expressed on the cell membrane of tumor cells, and in particular capable of interacting or binding to receptors expressed on the membrane of primary and/or disseminated or metastatic tumor cells. Also, antitumor drugs or therapeutic biomolecules can be encapsulated in said nanoemulsions and, finally, contrast agents can be incorporated for their use in the in vivo diagnosis in said nanoemulsions.

17 Claims, 17 Drawing Sheets

Specification includes a Sequence Listing.

(51) Int. Cl.
*A61K 49/00* (2006.01)
*A61K 51/12* (2006.01)
*A61P 35/00* (2006.01)

(56) References Cited

OTHER PUBLICATIONS

Desai A, Vyas T, Amiji M. Cytotoxicity and apoptosis enhancement in brain tumor cells upon coadministration of paclitaxel and ceramide in nanoemulsion formulations. Journal of pharmaceutical sciences. Jul. 1, 2008;97(7):2745-56. (Year: 2008).*

Carvalho et al., "Co-encapsulation of paclitaxel and C6 ceramide in tributyrin-containing nanocarriers improve co-localization in the skin and potentiate cytotoxic effects in 2D and 3D models," *European Journal of Pharmaceutical Sciences* 109:131-143, Jul. 2017. (13 pages).

Constantinides et al., "Formulation Development and Antitumor Activity of a Filter-Sterilizable Emulsion of Paclitaxel," *Pharmaceutical Research* 17(2):175-182, Feb. 2000. (8 pages).

Darfler, "Preparation and Use of Lipid Microemulsions as Nutritional Supplements for Culturing Mammalian Cells," *In Vitro Cellular & Developmental Biology* 26:779-783, Aug. 1990. (5 pages).

Ganta et al., "Development of EGFR-Targeted Nanoemulsion for Imaging and Novel Platinum Therapy of Ovarian Cancer," *Pharmaceutical Research* 31(9):2490-2502, Mar. 2014. (13 pages).

Ganta et al., "EGFR Targeted Theranostic Nanoemulsion For Image-Guided Ovarian Cancer Therapy," *Pharmaceutical Research* 32(8):2753-7563, Mar. 2015. (11 pages).

Ganta et al., "Nanoemulsions in Translational Research-Opportunities and Challenges in Targeted Cancer Therapy," *AAPS PharmSciTech* 15:694-708, Feb. 2014. (15 pages).

Gliszczyńska-Świgło et al., "Tocopherol Content in Edible Plant Oils," *Polish Journal of Food and Nutrition Sciences* 57(4A):157-161, Dec. 2007. (5 pages).

Hatziantoniou et al., "Scanning electron microscopy study on nanoemulsions and solid lipid nanoparticles containing high amounts of ceramides," *Micron* 38:819-823, 2007 [Published online Jul. 2007]. (5 pages).

Patel et al., "Design, Synthesis, and Characterization of Folate-Targeted Platinum-Loaded Theranostic Nanoemulsions for Therapy and Imaging of Ovarian Cancer," *Molecular Pharmaceutics* 13:1996-2009, May 2016. (14 pages).

Talekar et al., "Phosphatidylinositol 3-kinase Inhibitor (PIK75) Containing Surface Functionalized Nanoemulsion for Enhanced Drug Delivery, Cytotoxicity and Pro-apoptotic Activity in Ovarian Cancer Cells," *Pharmaceutical Research* 29:2874-2886, Jun. 2012. (13 pages).

Tiwari et al., "Improved oral delivery of paclitaxel following administration in nanoemulsion formulations," *Journal of Nanoscience and Nanotechnology* 6(9/10):3215-3221, Sep.-Oct. 2006. (7 pages).

Vezocnik et al., "Size fractionation and size characterization of nanoemulsions of lipid droplets and large unilamellar lipid vesicles by asymmetric-flow field-flow fractionation/multi-angle light scattering and dynamic light scattering," *Journal of Chromatography A* 1418: 185-191, Sep. 2015. (7 pages).

Wauson et al., "Amino acid regulation of autophagy through the Gpcr TASIR1-TASIR3," *Autophagy* 9(3):418-419, Mar. 2013. (2 pages).

Yilmaz et al., "Effect of lipid-containing, positively charged nanoemulsions on skin hydration, elasticity and erythema—An in vivo study," *International Journal of Pharmaceutics* 307:232-238, 2006 [Published online Nov. 2005]. (7 pages).

* cited by examiner

NANOSYSTEMS AS SELECTIVE VEHICLES

REFERENCE TO AN ELECTRONIC SEQUENCE LISTING

The contents of the electronic sequence listing (370093_402C1_SEQUENCE_LISTING.xml; Size: 15,293 bytes; and Date of Creation: Jan. 31, 2023) is herein incorporated by reference in its entirety.

FIELD OF THE TECHNIQUE

The present invention belongs to the medical field, in particular to the field of pharmacological vehicles with nanotheranostic potential, in particular for the approach to cancer and the management of primary tumors and metastatic disease, the encapsulation of antitumor drugs and/or, finally, for the incorporation of a contrast agent for its use in in vivo diagnosis.

BACKGROUND OF THE INVENTION

The present invention offers a new pharmacological tool with nanotheranostic potential.

A nanotechnology is a system that can combine elements of therapy and image in the same nanostructure which offers a series of advantages, among which is the possibility of monitoring the treatment in real time and thus be able to adjust the type and dosage of drug for each patient, in addition to facilitating the study of the biodistribution and accumulation of the drug using non-invasive imaging techniques such as positron emission tomography (PET) or magnetic resonance imaging (MRI). While PET requires a radioactive element, MRI uses a magnet capable of generating a constant magnetic field of great intensity. Therefore, this technique is applied to magnetic particles such as, for example, superparamagnetic iron oxide nanoparticles (SPIONs), whose function in taking images by MRI is to give a negative (dark) contrast, or other molecules such as gadolinium or perfluorocarbons.

In short, using nanometric systems associated with contrast agents, suitable ligands and/or the indicated drug, it is intended to reach a diagnosis—as early as possible—and a successful treatment through a single unit, the nanotheranostics.

As for the treatment through said single unit, the nanotheranostic, this type of structures could be especially useful in the treatment of tumors. In this sense, it is noted that although primary tumors are the triggers of different types of cancer, it is the subsequent events of tumor dissemination and metastasis formation that mainly determine the morbidity and mortality of patients, being the cause of 90% of deaths from human cancer. The metastases originate once the cancer cells have separated from the original (primary) tumor, traveled through the blood or lymphatic system, colonizing a new organ, and causing new tumors in other organs or tissues of the body. The metastatic tumor cells exhibit a phenotype that generally differs from the cells of the primary tumor, being generally more resistant, which, together with the distal location, makes their monitoring and treatment especially complicated. A possible solution is to identify this type of cells and eliminate them, before they proliferate uncontrollably. For this, the possibility of functionalizing nanoparticles is proposed, making them very selective and specific against tumor cells, in particular cells that have spread.

The present invention approaches this aspect by providing a nanotheranostic system that duly functionalized could facilitate the early detection and eradication not only of cells from the primary tumor but also of disseminated cells, providing an effective therapy against cancer. This system will also allow, after the association of a contrast agent, ligand and/or specific drugs, to reach a diagnosis—as early as possible—and/or a successful treatment through a single unit.

BRIEF DESCRIPTION OF THE INVENTION

In the present invention, the development of various oil-in-water (O/W) nanoemulsions containing an oil phase or oil core, preferably selected from vitamin E or oleic acid, stabilized by a sphingolipid of the sphingomyelin type, and optionally other lipids such as phospholipids, cholesterol, octadecylamine, DOTAP (N-[1-(2,3-Dioleoyloxy) propyl]-N,N,N-trimethylammonium methyl-sulfate), and PEGylated derivatives (derivatives with polyethylene glycol), for use as a nanotech vehicle, in particular for the management of cancer and metastatic disease is herein described. Said nanoemulsions can be functionalized with ligands capable of interacting or binding to receptors expressed on the cell membrane of tumor cells, and in particular capable of interacting or binding to receptors expressed on the membrane of primary and/or disseminated or metastatic tumor cells. Also, antitumor drugs or therapeutic biomolecules can be encapsulated in said nanoemulsions and, finally, contrast agents can be incorporated for their use in the in vivo diagnosis in said nanoemulsions.

Additionally, the authors of the present invention have identified in CTCs (circulating tumor cells) and in tumors, several receptors of interest for the selective direction of nanostructures, such as, for example, the leptin receptor, the guanylyl cyclase receptor, or other molecules of the tumor, or of the tumor microenvironment, such as integrins and laminin, against which it is possible to direct these nanoemulsions, previous functionalization with ligands capable of mediating a selective interaction, having shown that once the oil-in-water nanoemulsions have been functionalized (O/W) of the present invention, containing an oil phase, preferably selected from vitamin E or oleic acid, a sphingolipid of the sphingomyelin type and optionally other lipids such as phospholipids, cholesterol, octadecylamine, DOTAP, and PEGylated derivatives, with ligands to this receptor, observe an intracellular accumulation of said nanoemulsions in a more efficient manner in primary, disseminated and metastatic tumor cells, preferably in metastatic cells having these receptors and/or molecules. This discovery opens the doors to the functionalization of any type of nanosystem with a compound of the group selected from the list consisting of antibodies, fragments of antibodies, aptamers, peptides, or hydrophobic or hydrophilic molecules of small molecular weight, such as lactisole, as well as ligand-drug or ligand-radioisotope conjugates, capable of binding to these receptors and/or molecules, for use as pharmacological vehicles and/or diagnostics against tumor cells, in particular against CTCs (circulating tumor cells) and against to primary, disseminated or metastatic tumor cells.

Figure 1A:
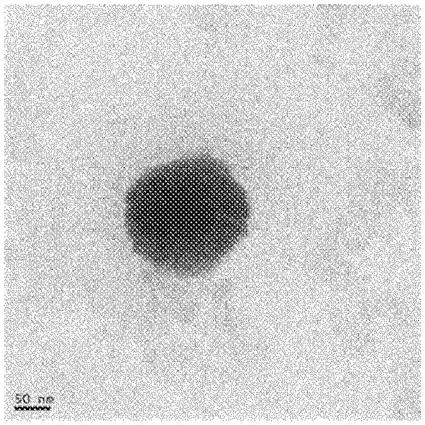
FIGS. 1A and 1B. Images acquired by transmission electron microscopy of sphingomyelin (SM) and vitamin E (V) nanoemulsions, prepared with a ratio V:SM 1:0.1 (FIG.
Figure 1B:
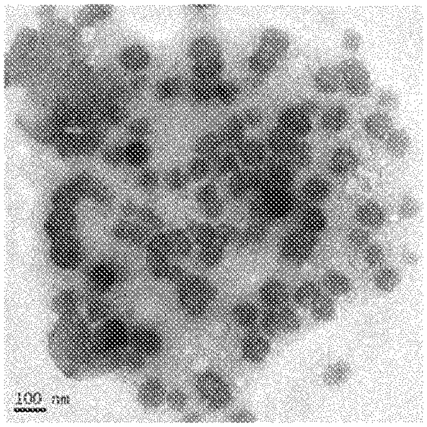

1A), and a population of nanoemulsions that also incorporate octadecylamine (OCT) V:SM:OCT 1:0.1:0.01 (FIG. 1B).

Figure 2A:
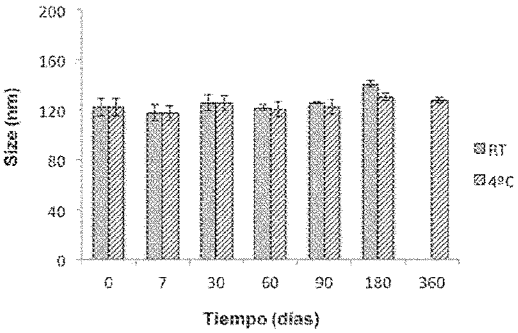
Figure 2B:
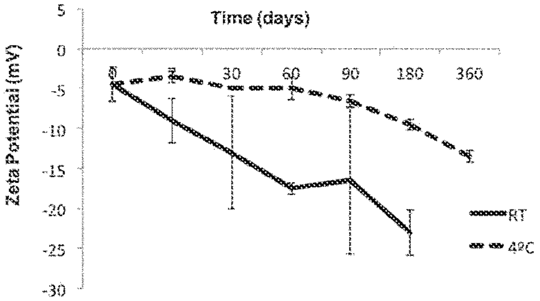
Figure 2C:
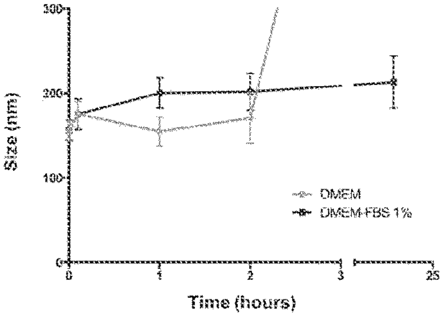
Figure 2D:
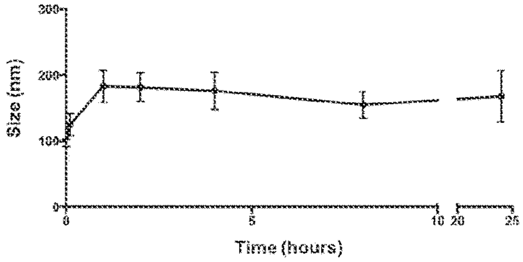

FIGS. 2A, 2B, 2C and 2D. Stability of nanoemulsions based on sphingomyelin (SM) and vitamin E (V), at a ratio V:SM 1:0.1, regarding particle size (FIG. 2A) and surface charge (FIG. 2B) for 6 months at room temperature and for one year at 4° C. Stability of this same formulation after incubation in culture medium and culture medium supplemented with FBS (FIG. 2C) and in human plasma (FIG. 2D).

Figure 3A:
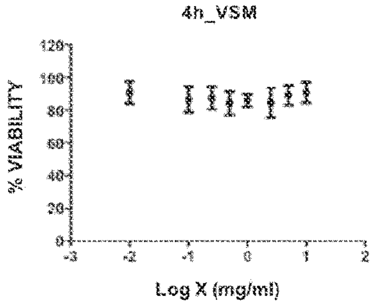
Figure 3B:
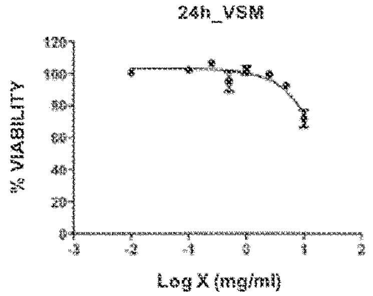
Figure 3C:
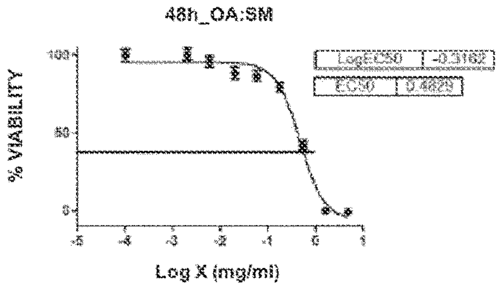
Figure 3D:
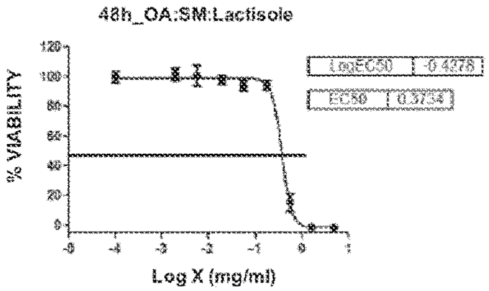
Figure 3E:
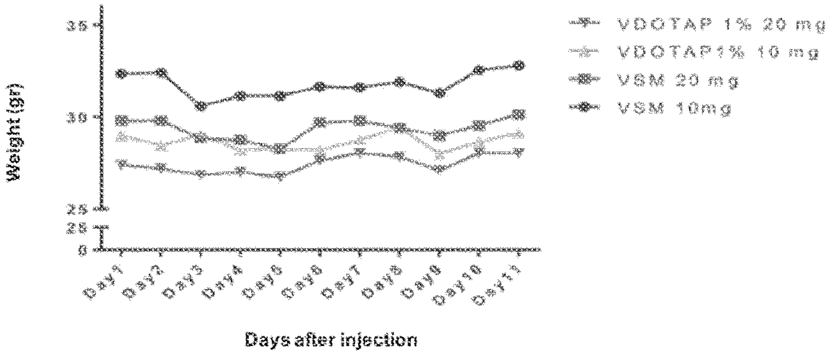

FIGS. 3A, 3B, 3C, 3D and 3E. Cell viability assay (MTT) of nanoemulsions with different compositions VSM (vitamin E and sphingomyelin 1:0.1), several incubation times (4 h and 24 h) in SW480 cells (FIG. 3A and FIG. 3B), MTT test of nanoemulsions of oleic acid and sphingomyelin without ligand (OA:SM 1:0.1) and with lactisole (OA:SM:Lact 1:0.1:0.1), after 48 h of incubation in SVV620 cells (FIG. 3C and FIG. 3D). Study of the tolerated dose based on the weight of the mice that received serial intravenous injections of nanoemulsions VSM (vitamin E and sphingomyelin, 1:0.1) and VSM with DOTAP (VDOTAP 1%) at two concentrations (10 mg/ml and 20 mg/ml). There are no changes in weight that could indicate acute toxicity or physiological or apparent behavior changes during the observation period (FIG. 3E).

Figure 4A:
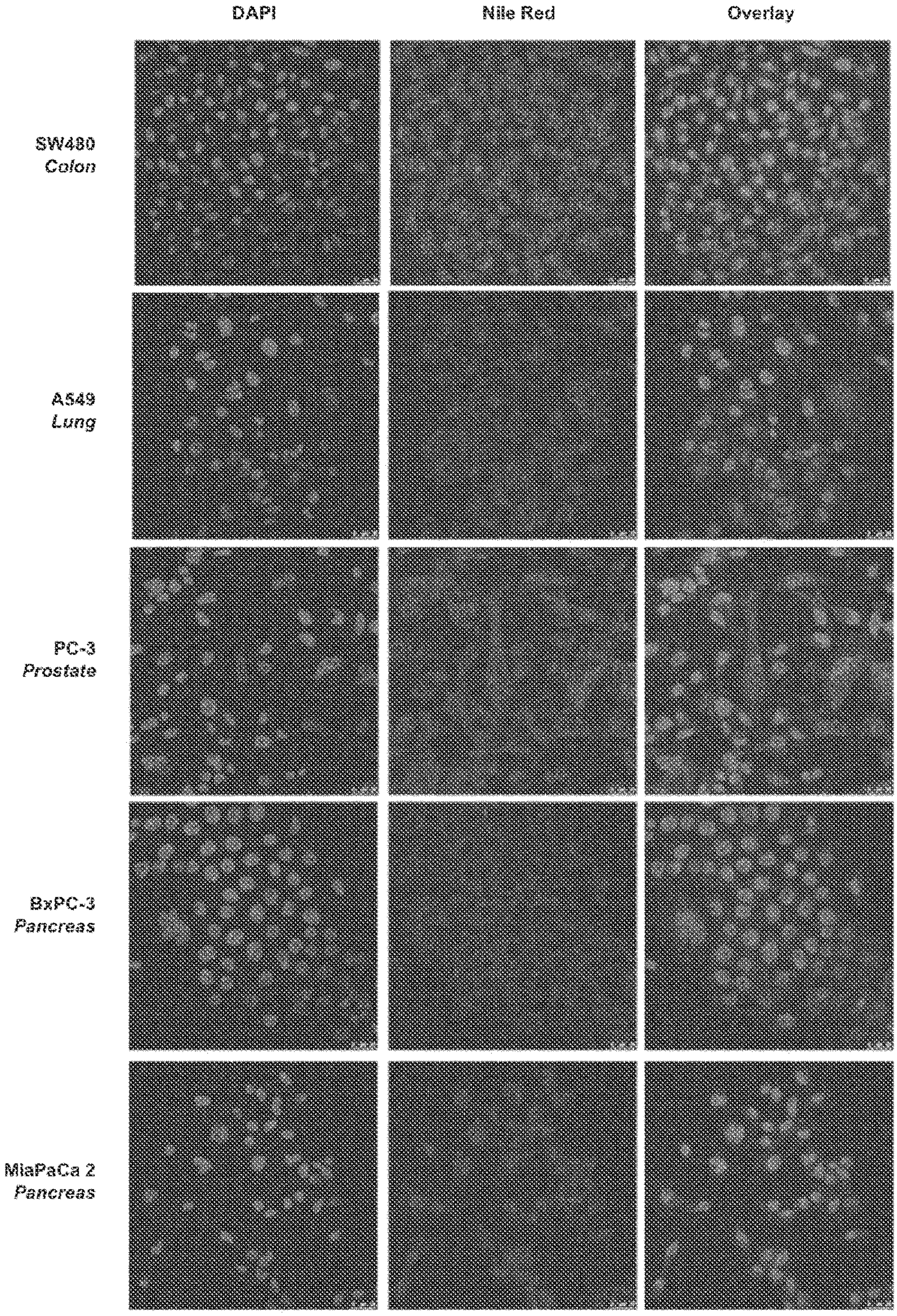
Figure 4B:
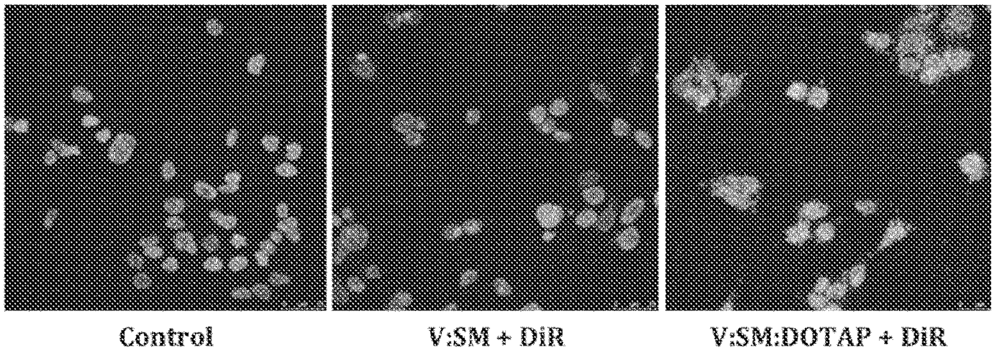
Figure 4C:
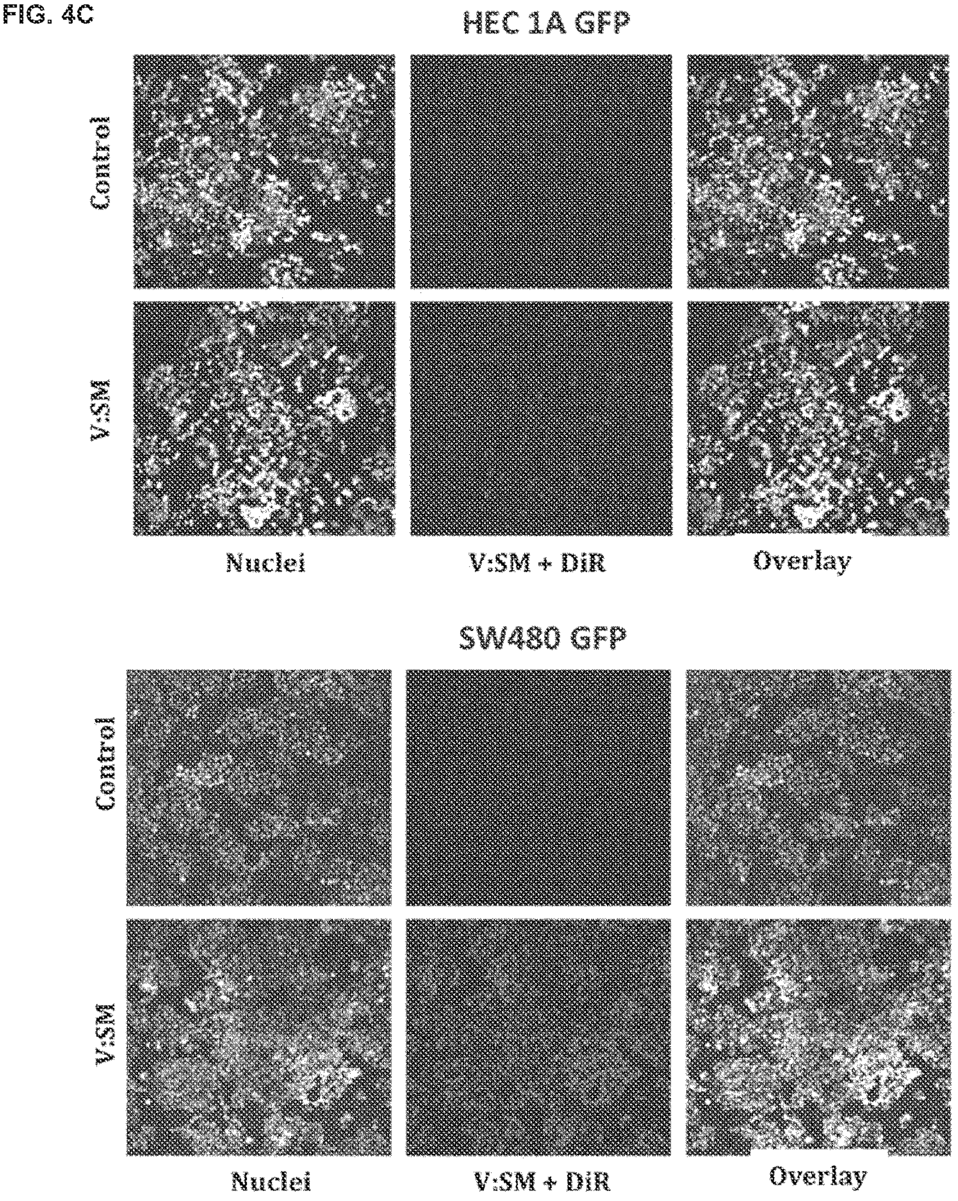

FIGS. 4A, 4B and 4C. Nanoemulsions of vitamin E and sphingomyelin (V:SM 1:0.1) with Nile Red encapsulated, and incubated with tumor cells of different origins (colon, lung, prostate and pancreas), and observed under the confocal microscope (the Dapi channel corresponds to the nuclei and the Nile Red channel with the nanoemulsions) (FIG. 4A). V:SM 1:0.1 and V:SM:DOTAP 1:0.1:0.1 with DiR encapsulated, incubated with colon tumor cells (HTC116), and observed under a confocal microscope (nanoemulsions can be observed as white dots around the cell nucleus) (FIG. 4B) and V:SM 1:0.1 with DiR encapsulated and incubated with endometrial tumor cells (HEC1A) and colon (SW480) that have been previously transformed to express GFP, and observed under the confocal microscope (the Nile Red channel corresponds to the nanoemulsions and that of the GFP to the cellular cytoplasms) (FIG. 4C).

Figure 5A:
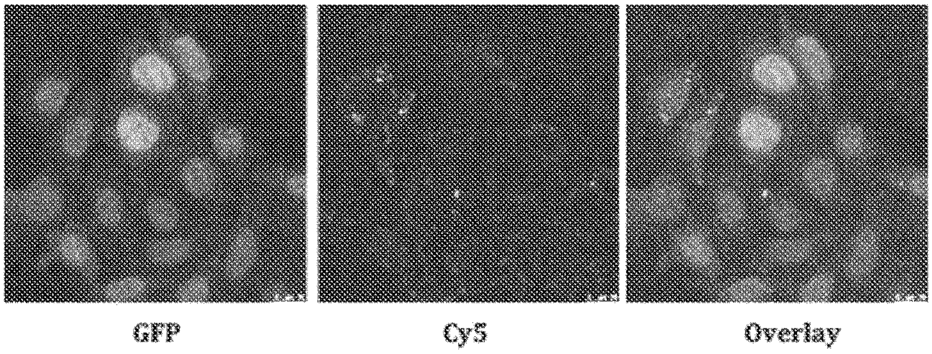
Figure 5B:
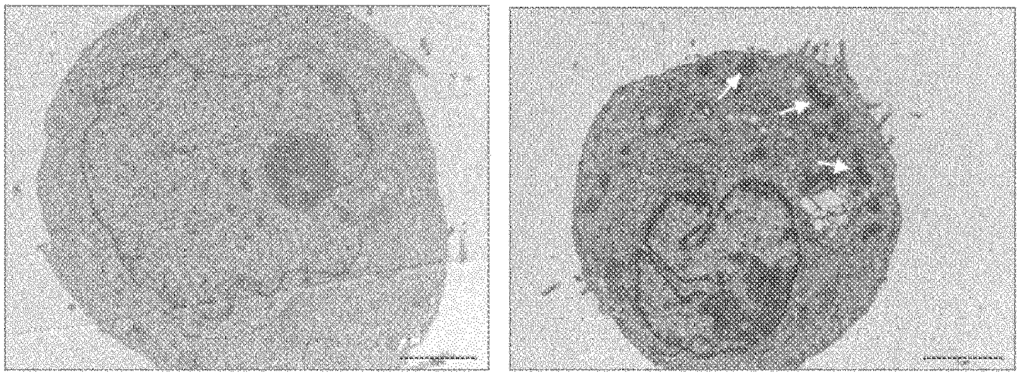

FIGS. 5A and 5B. Sphingomyelin nanoemulsions (V:SM 1:0.1) that encapsulate fluorescent RNA (Cy5-RNA), incubated with colon tumor cells previously transformed to express GFP (HCT116-GFP), and observed under the confocal microscope (the channel of the GFP corresponds to the cells and that of Cy5 is attributed to the RNA transported by the nanoemulsions (FIG. 5A). Images of transmission electron microscopy of SW620 cells treated with nanoemulsions of oleic acid and sphingomyelin functionalized with lactisole (O:SM:Lact 1:0.1:0.1), that encapsulate magnetic nanoparticles, observing a corresponding contrast signal in the vacuoles that have been originated at the cellular cytoplasm level (image on the right, arrows indicate the location), which it is not seen in control cells (untreated, image on the left) (FIG. 5B).

Figure 6A:
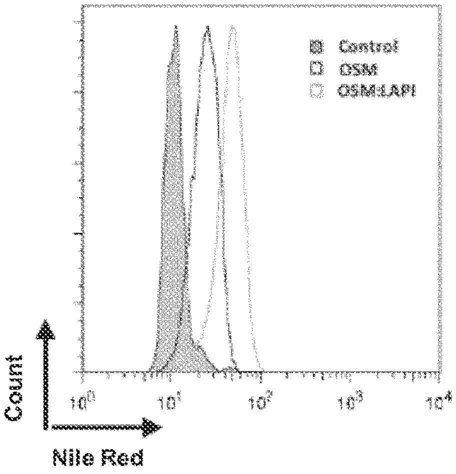
Figure 6B:
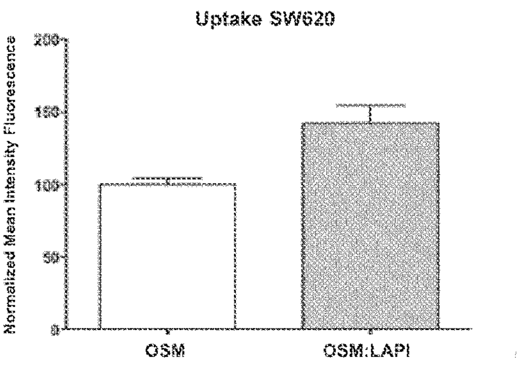

FIGS. 6A and 6B. Internalization of fluorescent nanoemulsions evaluated by flow cytometry. The fluorescence intensity of colon tumor cells (SVV620), positive for Nile Red encapsulated in nanoemulsions of oleic acid and sphingomyelin is greater when it comes to nanoemulsions functionalized with LAPI (OSM-LAPI; O:SM:LAPI 1:0,1:0.01 clear line), with respect to the non-functionalized nanoemulsions (OSM, O:SM 1:0.1, dark line) (FIG. 6A). Bar graph representation of the average fluorescence intensity obtained in the cytometer (FIG. 6B).

Figure 7:
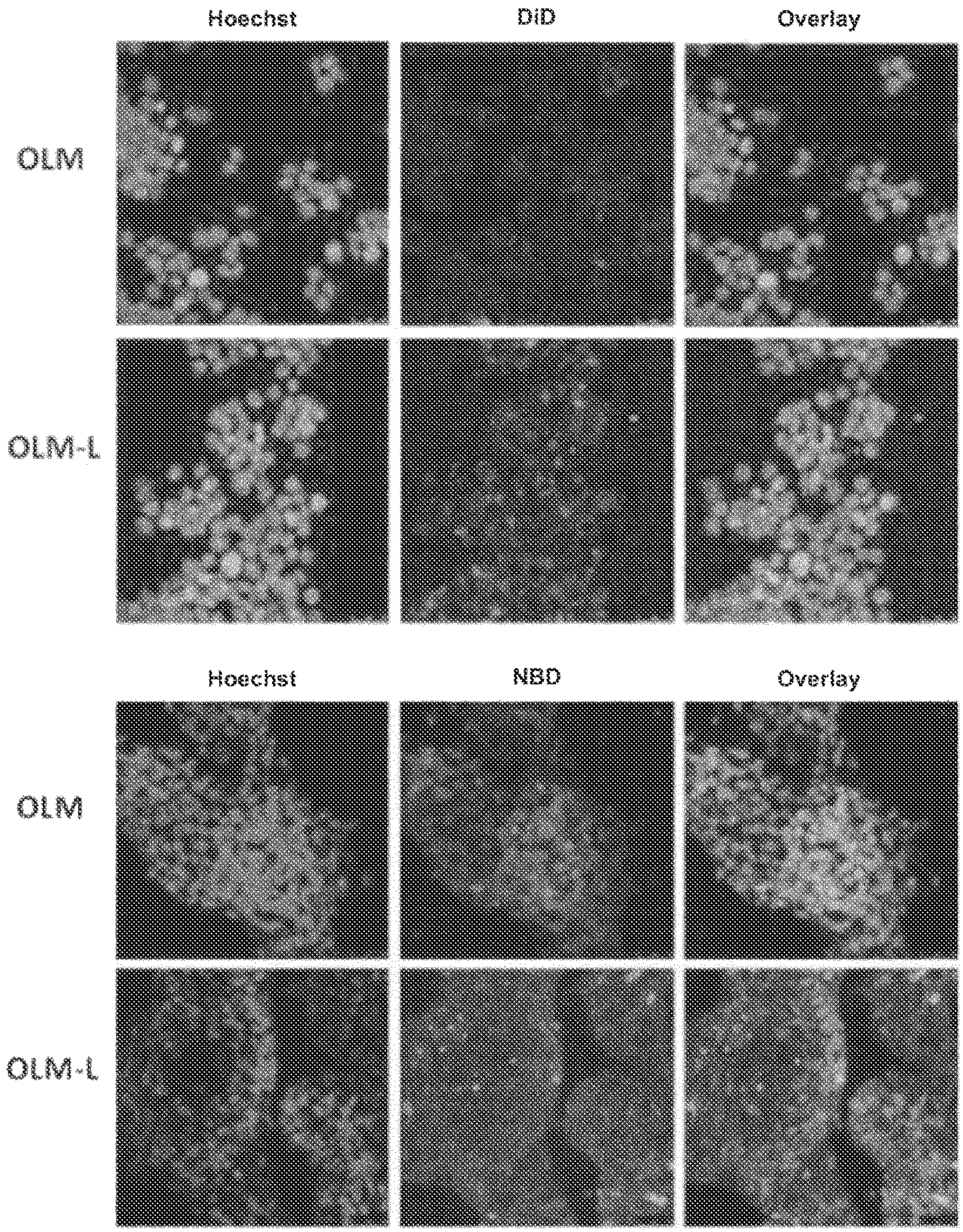

FIG. 7. Confocal microscopy images of colon tumor cells (SW620) treated with nanoemulsions of oleic acid and a derivative of sphingomyelin labeled with NBD, which also encapsulate DiR (OLM; O:SM 1:0.1), and those same functionalized nanoemulsions with lactisole (OLM-L; O:SM:Lact 1:0.1:0.1). The cell nuclei are stained with Hoechst. A greater intensity of the signal (corresponding to the sphingomyelin labeled with NBD and to the encapsulated DiD) is observed in the case of functionalized nanoemulsions.

Figure 8:
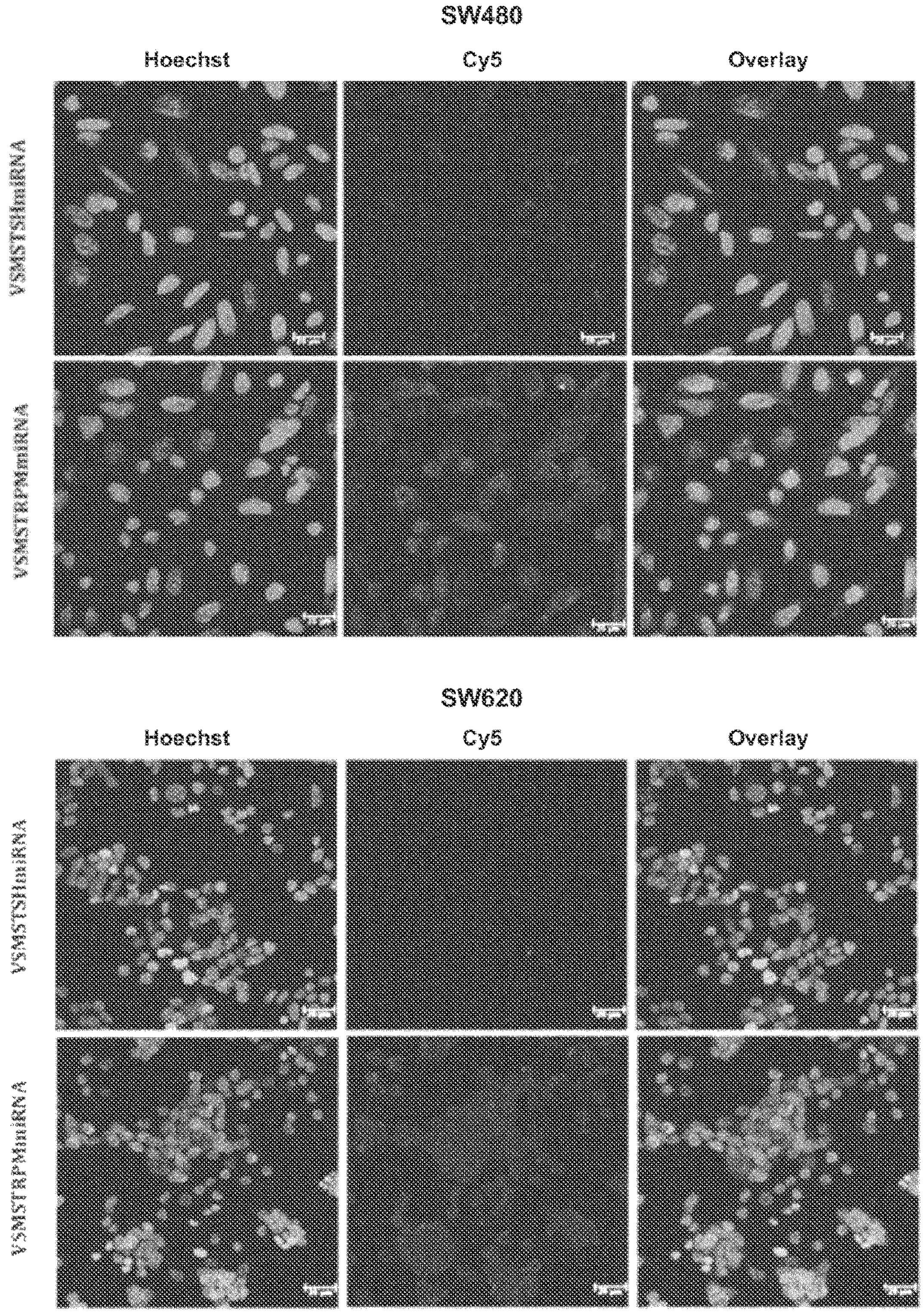

FIG. 8. Confocal microscopy images of colon tumor cells (SW480 and SW620) treated with nanoemulsions of vitamin E, sphingomyelin and oactadecylamine (V:SM:OCT 1:0.1:0.01) functionalized with RPM (VSMSTRPM) and non-functionalized control formulations (VSMSTSH), to which labeled miRNA has been associated with Cy5 fluorophore. A greater intensity of fluorescence due to the internalization of the miRNA is observed for those functionalized formulations (VSMSTRPMmiRNA), in both cell lines (the Hoechst channel corresponds to the cell nuclei and that of the Cy5 with the miRNA associated with the nanoemulsions).

Figure 9A:
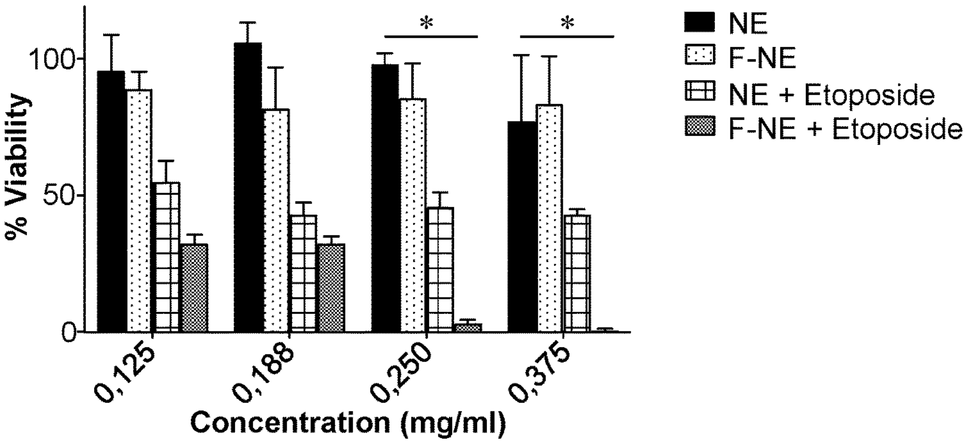
Figure 9B:
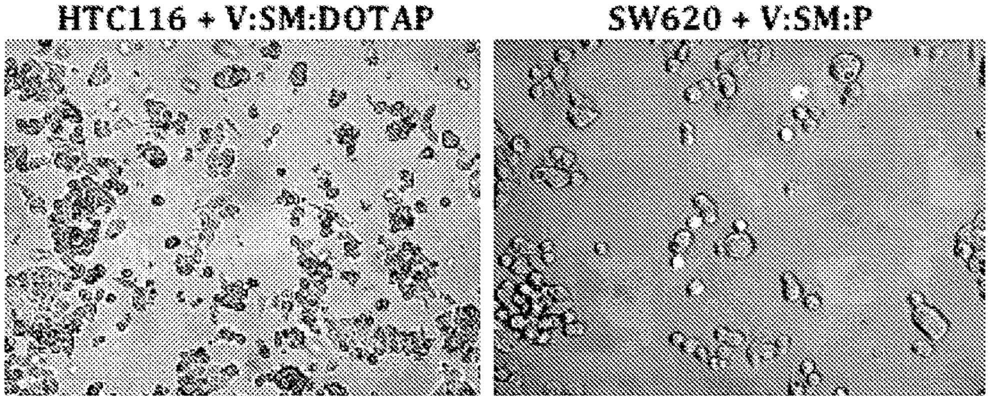
Figure 9C:
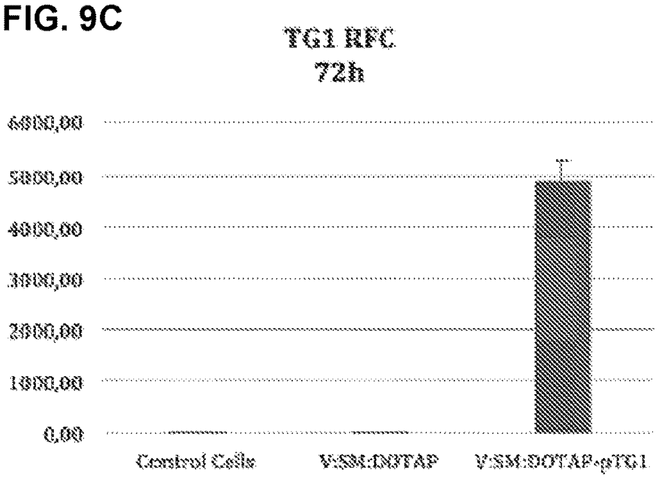
Figure 9D:
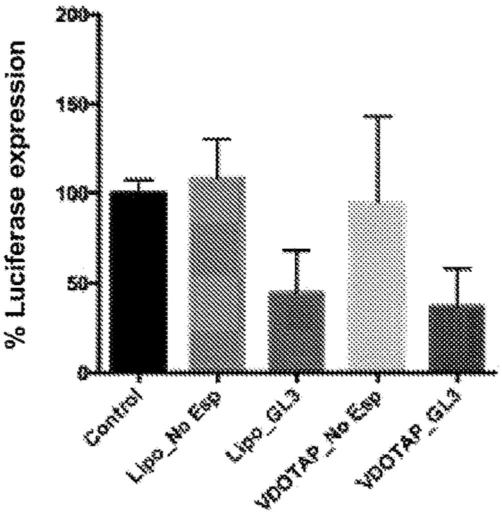

FIGS. 9A, 9B, 9C and 9D. Cell viability (MTT assay) of colon tumor cells (SW620) after being treated with nanoemulsions of oleic acid and sphingomyelin (O:SM 1:0.1, NE) and nanoemulsions functionalized with lactisole (O:SM 1:0.1, F-NE), blanks or encapsulating the antitumor drug etoposide, after 48-hour incubation (FIG. 9A). Expression of mCherry (bright white spots) in HTC116 cells transfected with pDNA-mCherry associated with nanoemulsions of sphingomyelin, vitamin E and DOTAP (V:SM:DOTAP 1:0.1:0.1) (image on the left), and in SW620 cells transfected with pDNA-mCherry associated with nanoemulsions of sphingomyelin, vitamin E and putrescine (V:SM:P 1:0.1:0.1) (image on the right), 24 hour post-transfection (FIG. 9B). Expression of P53TG1 LncRNA in HCT116 cells transfected with pTG1 associated with nanoemulsions V:SM:DOTAP (V:SM:DOTAP-pTG1), normalized with respect to GAPDH (2^-ddct) (FIG. 9C). Expression of luciferase in HTC116-LUC cells. Silencing is observed in the case of cells transfected with lipofectamine and siRNA anti luciferase (Lipo_GL3), and those transfected with V:SM:DOTAP (VDOTAP_GL3), but not with the non-specific siRNA sequences (No Esp) (FIG. 9D).

Figure 10A:
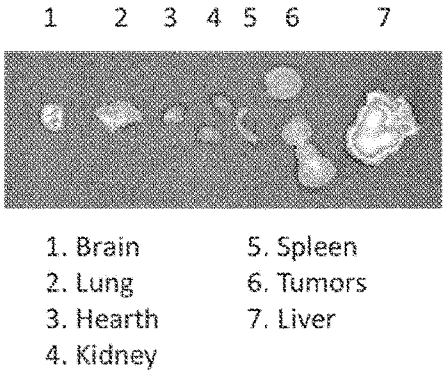
Figure 10B:
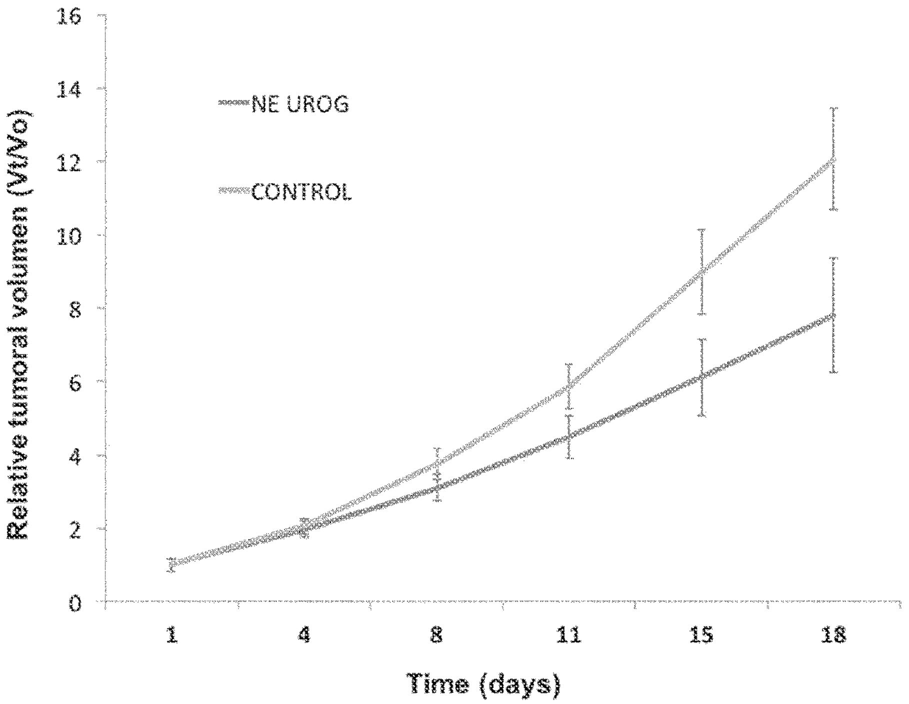

FIGS. 10A and 10B. Biodistribution study of sphingomyelin nanoemulsions decorated with uroguanylin (O:SM:UROG 1:0.1:0.01) and loaded with DiR, in mice that have developed a tumor after inoculation of colorectal cancer cells SW620 in both flanks. 24 hours after intravenous injection, the animals were sacrificed and the organs excised for observation in an optical imaging equipment (IVIS) (FIG. 10A). Tumor growth in mice implanted subcutaneously with colorectal cancer cells SW620. The mice were randomly divided into 2 groups. GROUP 1: control animals, which have not received treatment (clear line). GROUP 2: Animals treated with etoposide encapsulated in sphingomyelin nanoemulsions decorated with uroguanylin (NE UROG, dark line), administered intravenously (4 injections on days 1, 4, 8 and 11, dose: 0.2 mg etoposide/Kg) (FIG. 10B).

Figure 11:
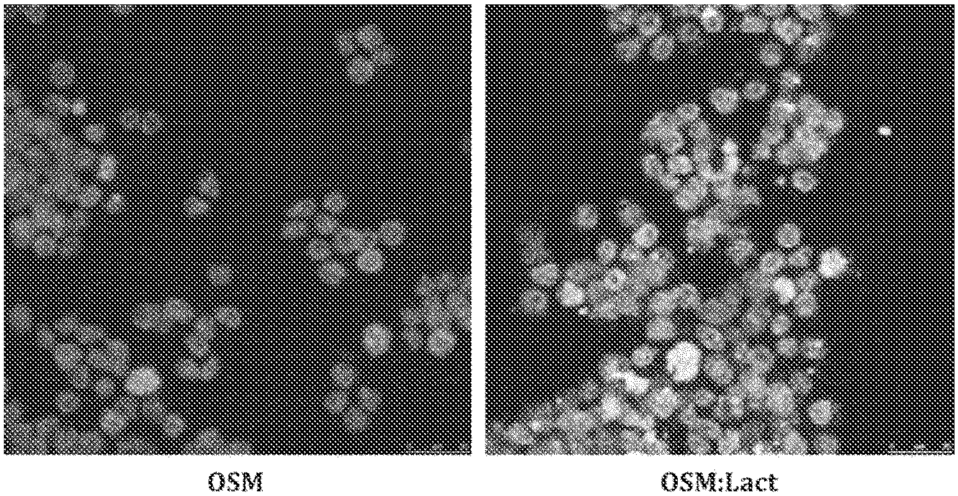

FIG. 11. Internalization of sphingomyelin nanoemulsions (O:SM 1:0.1) and those functionalized with lactisole (O:SM:Lact 1:0.1:0.1), labeled with DiR and incubated for 4 hours in SW620 tumor cells with elevated expression of TAS1R3. The fluorescence intensity is higher than in the case of nanoemulsions functionalized with lactisole. The cell nuclei are stained with DAPI and the clearest signal is attributed to DiD, encapsulated within the nanoemulsions.

Figure 12A:
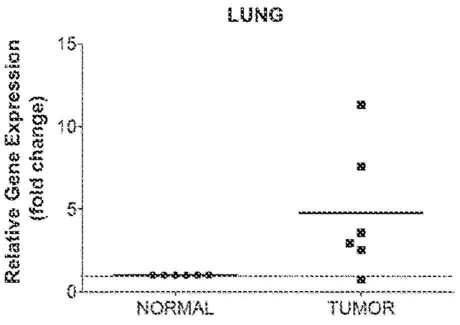
Figure 12B:
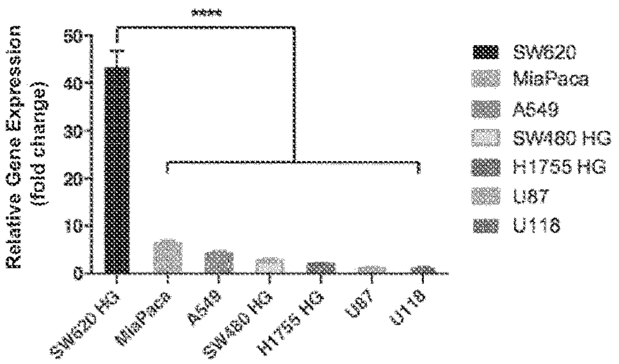
Figure 12C:
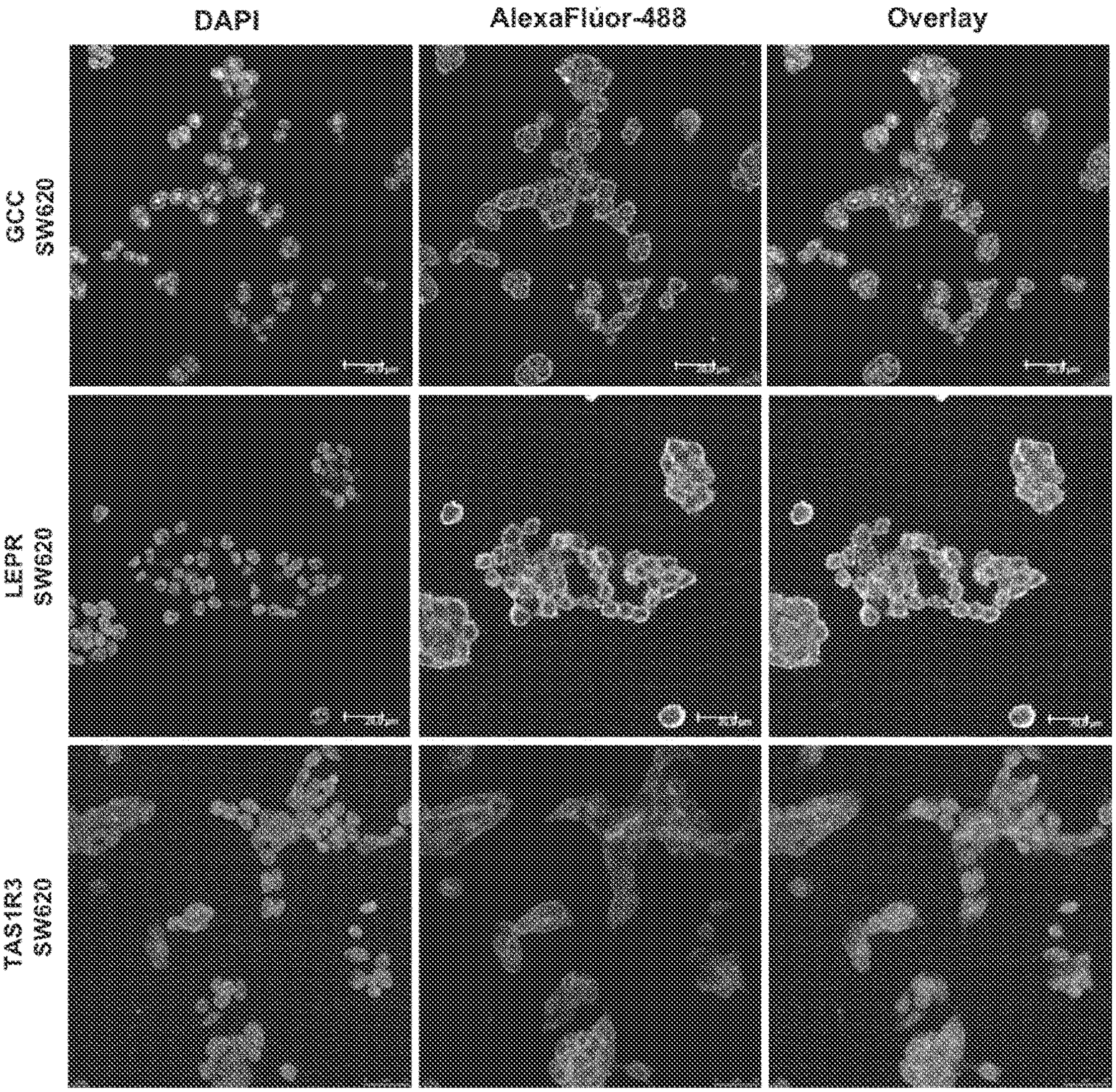
Figure 12C:
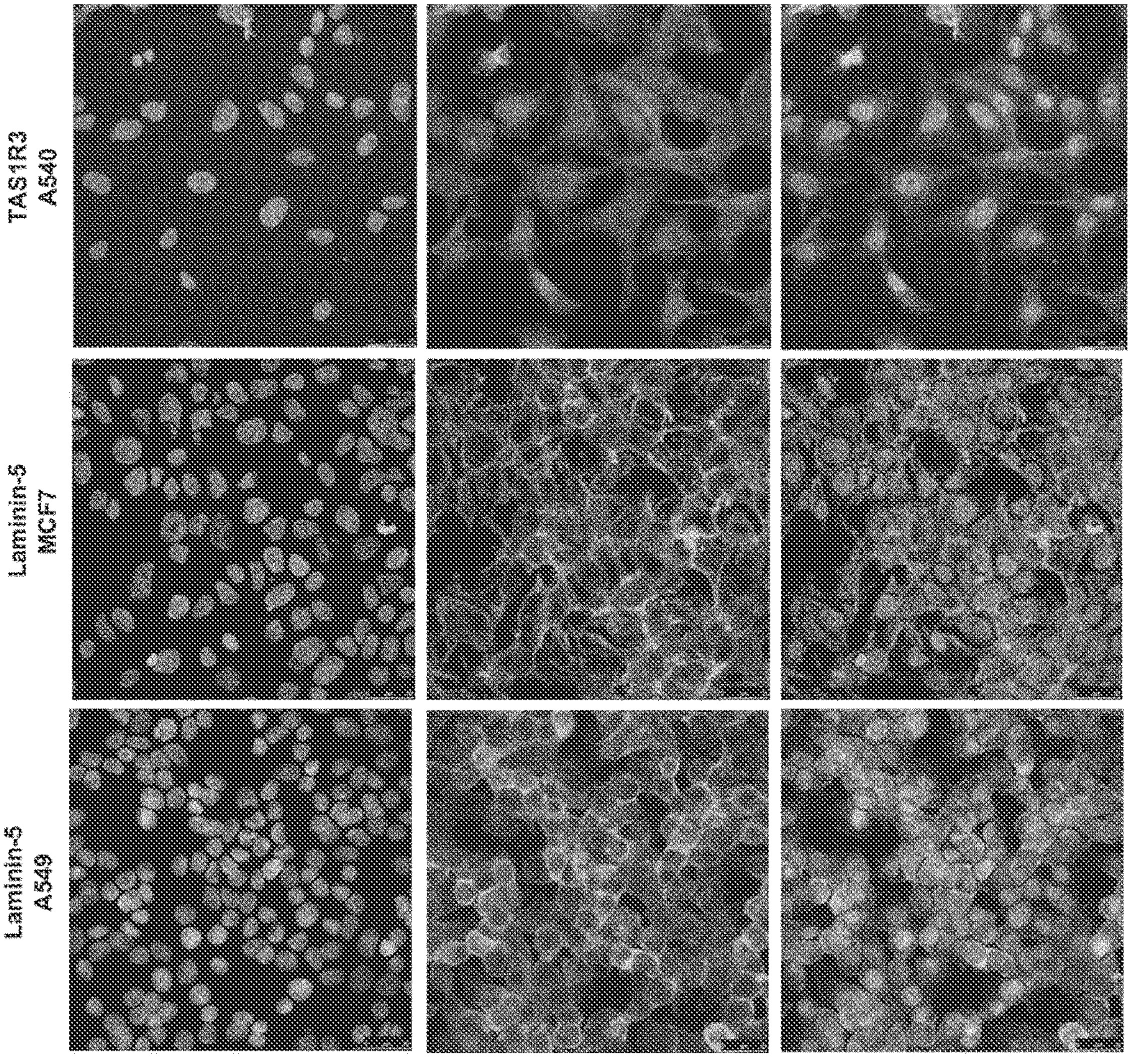

FIGS. 12A, 12B and 12C. Expression of TAS1R3 in tumor tissue of patients with metastatic lung cancer (NSCLC), versus non-tumor control tissue (n=6) (FIG. 12A). Relative expression of the TAS1R3 receptor (mRNA) in different cell lines of different tumor types, colon (SW620 and SW480), lung (A549 and H1755), glioblastoma (U87 and U118), and pancreas (MiaPaCa2) (P-value=0.0001) (FIG. 12B). Study of the expression of the different receptors (GCC, LEPR, TAS1R3 and Laminin-5) by immunofluorescence (clear signal) in a panel of tumor cells of different origin, colorectal cancer SW620, lung A549 and breast MCF7 (FIG. 12C).

Figure 13:
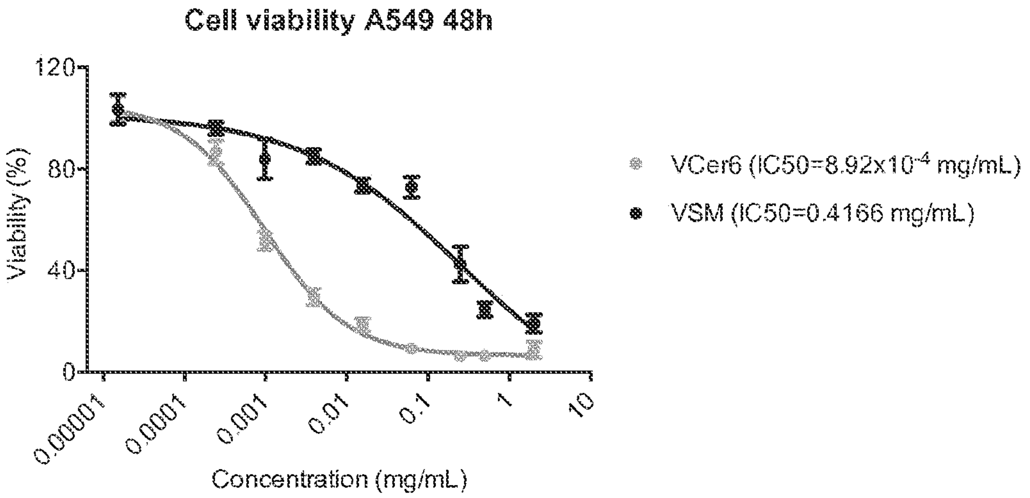

FIG. 13. This figure shows the cell viability/toxicity of the nanoemulsions of the invention. It shows a comparative assay wherein nanoemulsions comprising vitamin E+sphingomyelin (VSM) are compared with nanoemulsions comprising vitamin E+ceramide (VCer6). Such as it can be seen in this figure, the toxicity of the nanoemulsions comprising ceramide is significantly higher. V: vitamin E; SM: sphingomyelin; Cer6: ceramide C6.

Figure 14:
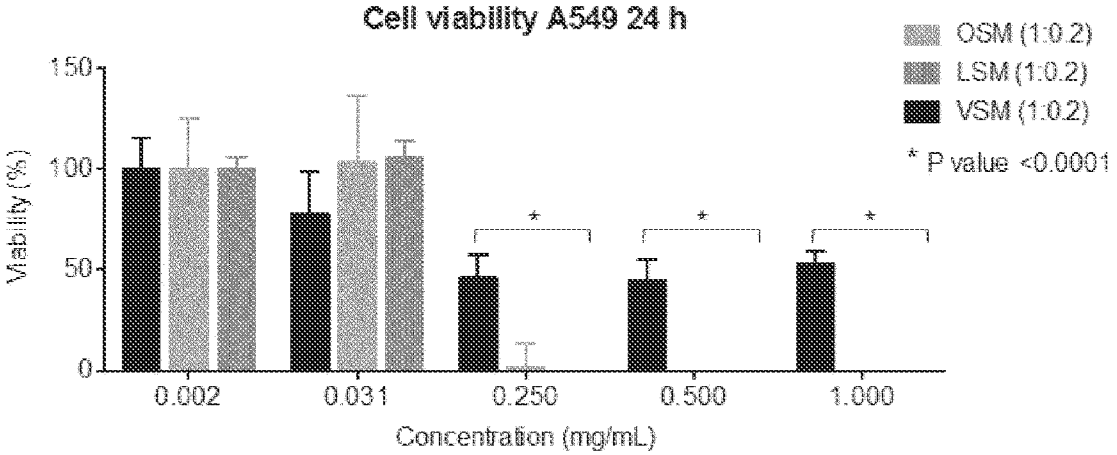

FIG. 14. This figure shows the cell viability/toxicity of the nanoemulsions of the invention. It shows that not all the oily nucleus are equally suitable for obtaining non-toxic theranostic nanoemulsions. The combination of sphingomyelin with linoleic acid (L) or with oleic acid (O) demonstrates that the use of oily nucleus such as linoleic acid (L) or oleic acid (O) is highly toxic. Such toxicity is significantly reduced when vitamin E is used. V: vitamin E; SM: sphingomyelin; O: oleic acid; L: linoleic acid.

Figure 15A:
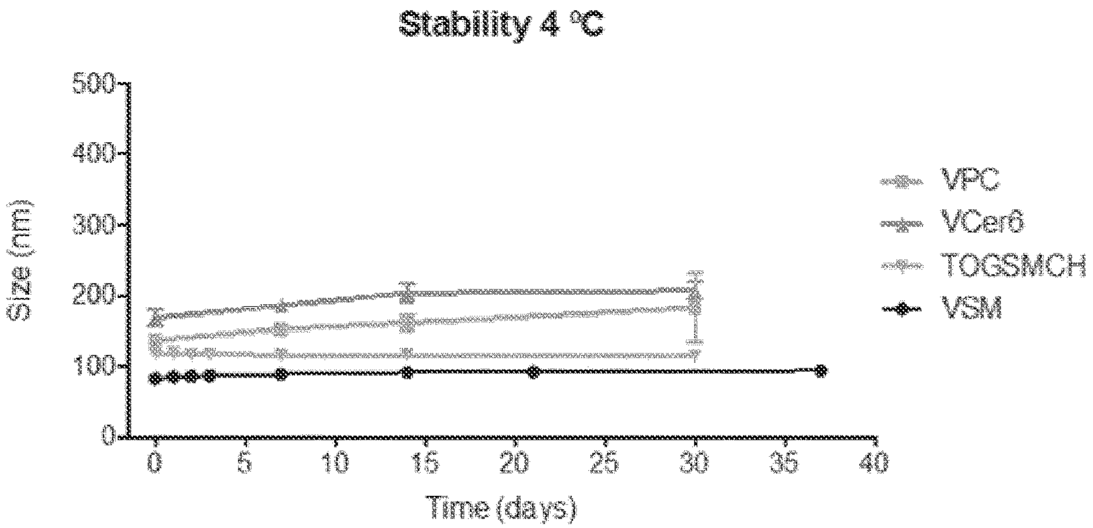
Figure 15B:
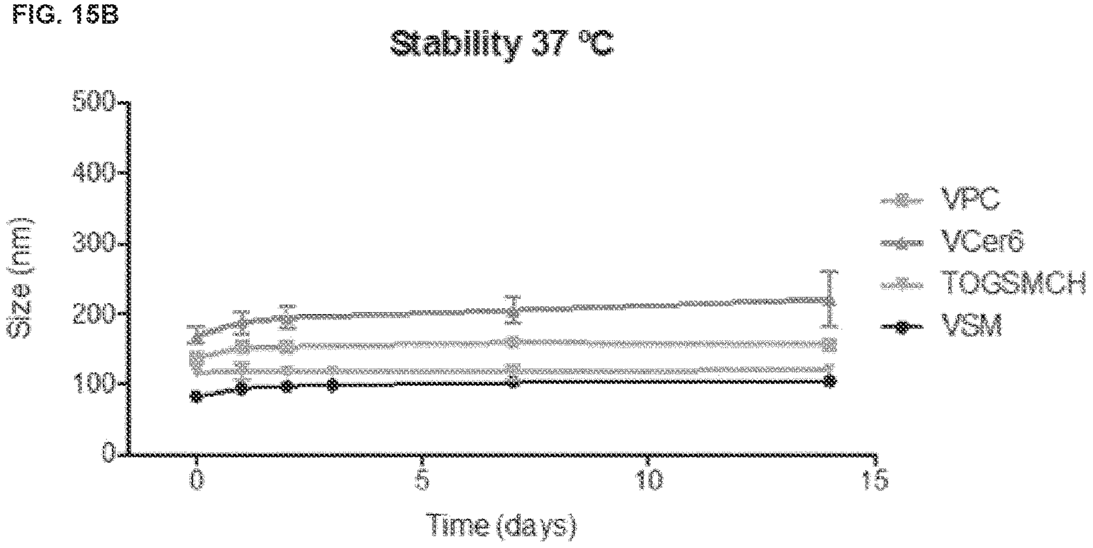
Figure 15C:
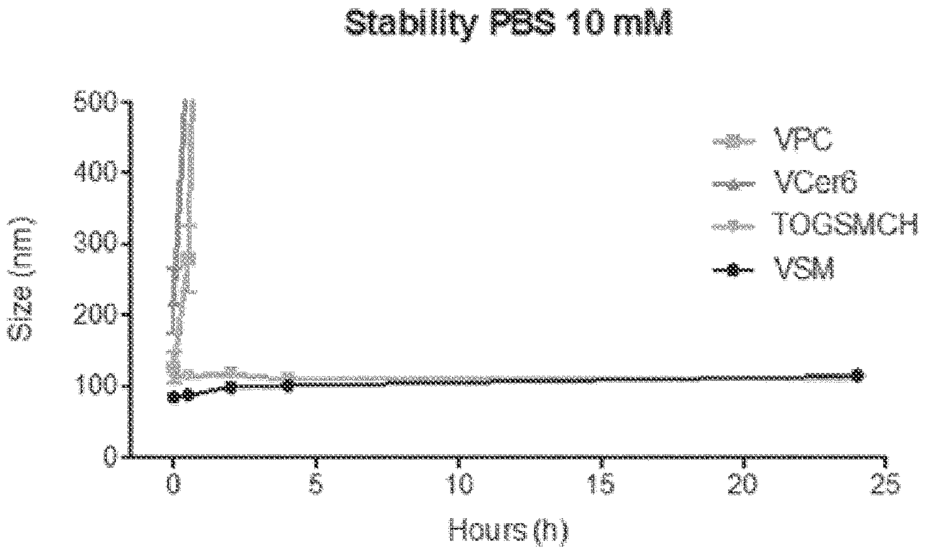
Figure 15D:
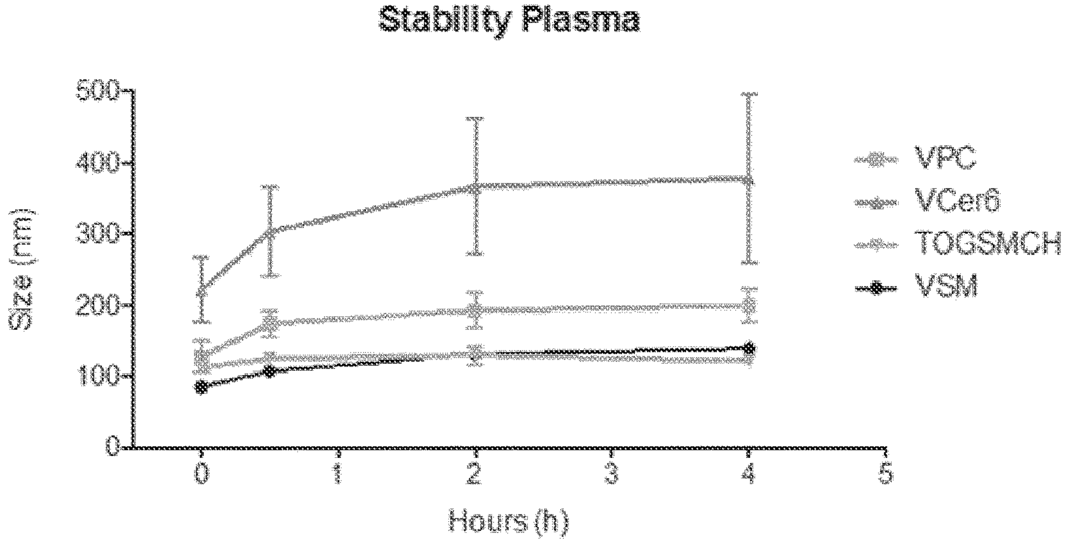

FIGS. 15A, 15B, 15C and 15D. This figure shows the stability of the nanoemulsions of the invention. It shows comparative tests showing the stability of different nanoemulsions. Particularly, the stability of the following nanoemusions were compared: Vitamin E+phosphatidylcholine (V:PC). Vitamin E+ceramide (V:Cer6). Triglycerides+sphingomyelin+colesterol (TOG:SM:CH). Vitamin E+sphingomyelin (V:SM), in different conditions. FIG. 15A (Stability 4° C.). FIG. 15B (Stability 37° C.). FIG. 15C (Stability PBS 10 mM). FIG. 15D (Stability plasma). Such as it can be seen in the figures, the nanoemulsion comprising sphingomyelin are more stable both during storage and in saline and plasma media, as compared with the nanoemulsions comprising other sphingolipids like ceramide, or a phospholipid like phosphatidylcholine. Vitamin E+phosphatidylcholine (VPC).Vitamin E+ceramide (VCer6). Triglycerides+sphingomyelin+colesterol (TOGSMCH). Vitamin E+sphingomyelin (VSM).

Figure 16A:
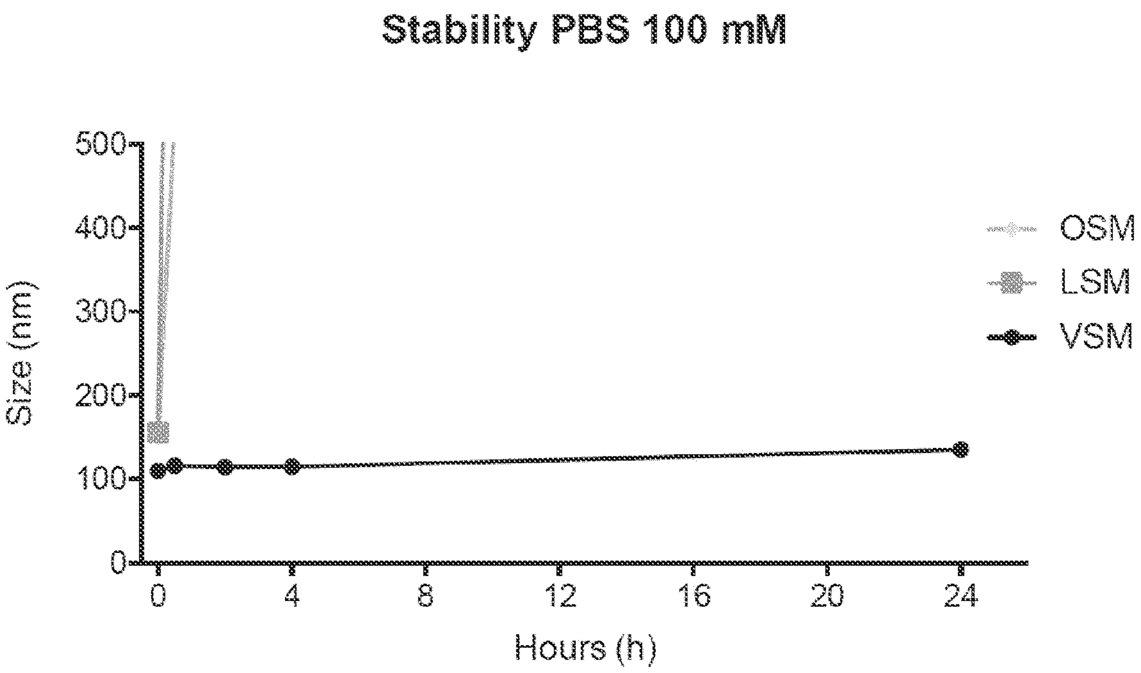
Figure 16B:
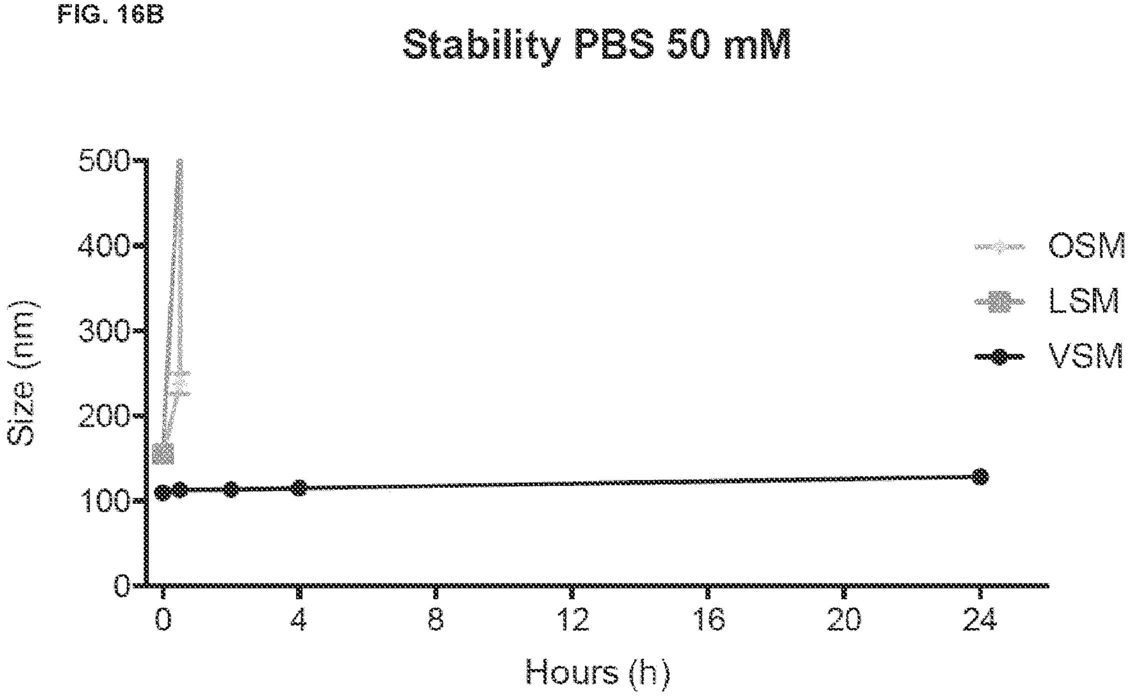
Figure 16C:
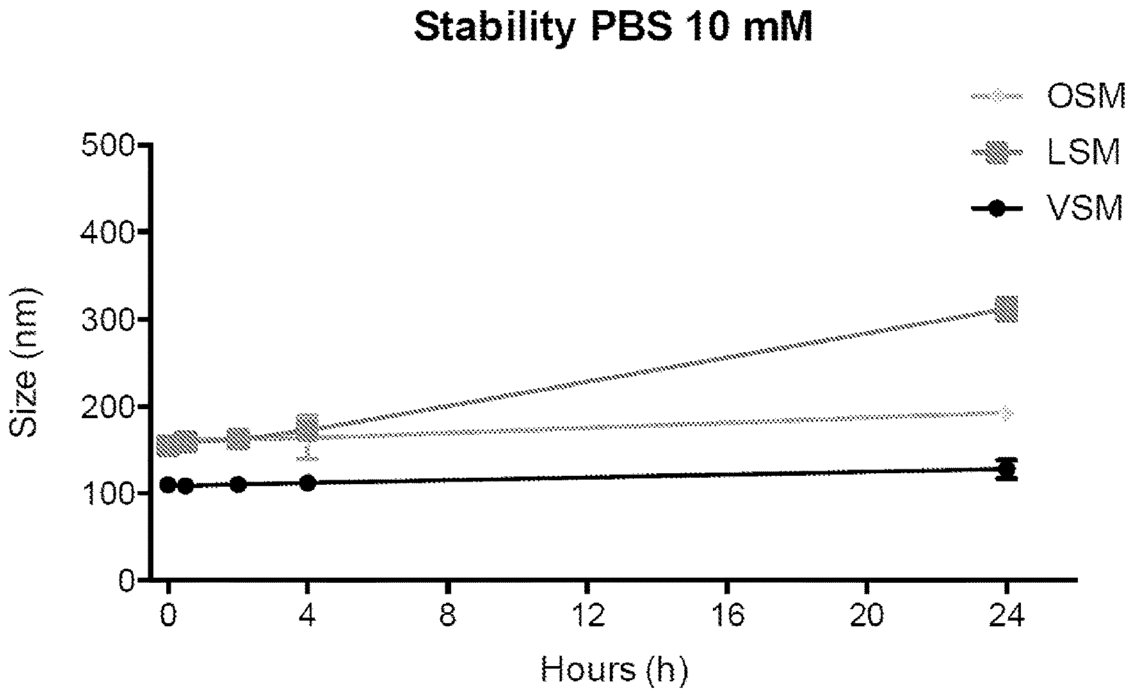

FIGS. 16A, 16B and 16C. This figure shows the stability of the nanoemulsions of the invention. It shows comparative tests regarding the stability of different nanoemulsions all of them comprising sphingomyelin and different oily nucleuses. FIG. 16A (Stability PBS 100 mM). FIG. 16B (Stability PBS 50 mM). FIG. 16C (Stability PBS 10 mM). Interestingly, the stability of those nanoemulsions comprising a linoleic or oleic acid nucleus is clearly diminished in comparison to the stability shown when vitamin E is used. V: vitamin E; SM: sphingomyelin; O: oleic acid; L: linoleic acid.

Figure 17:
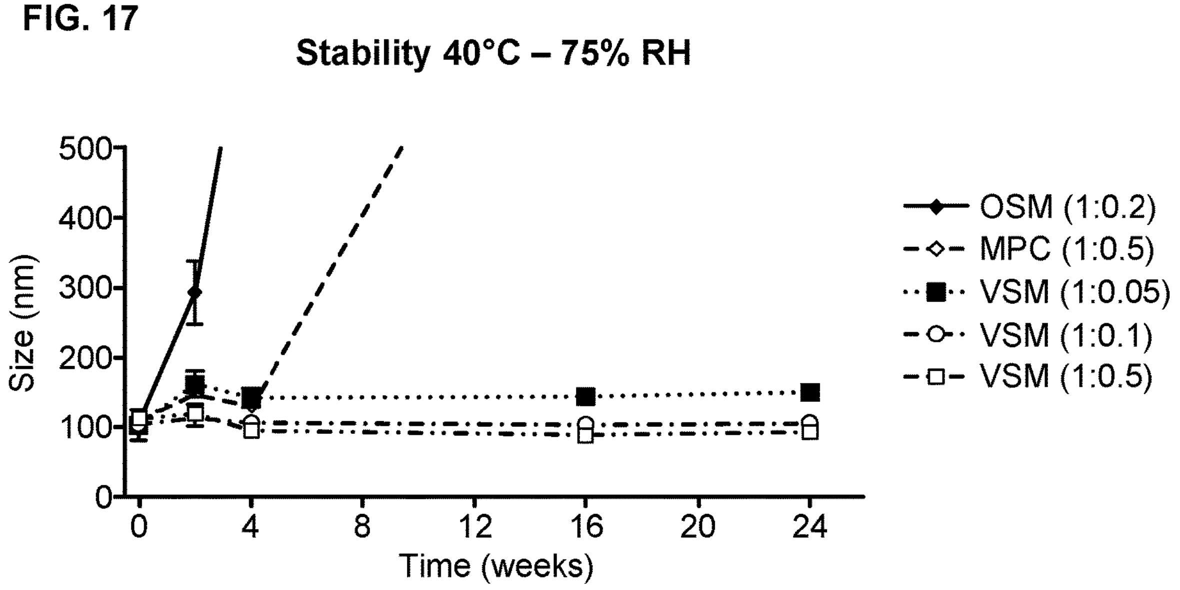

FIG. 17. This figure shows the stability of the nanoemulsions of the invention. It shows that, under stress conditions at 40° C. and 75% humidity (conditions required or mandatory for regulatory approval), those nanoemulsions having an oleic acid nucleus (OSM) or a different oily nucleous (Migliol) and surfactant (phosphatidylcholine) are clearly inestable, whereas those nanoemulsions comprising vitamin E and sphingomyelin are stable. V: vitamin E; SM: sphingomyelin; O: oleic acid; PC: phosphatidylcholine; M: Mygliol.

DETAILED DESCRIPTION OF THE INVENTION

Definitions

In the present invention "nanoemulsion" is understood to be structures composed of an oil or mixtures of oils, dispersed in water as droplets of nanometric size, and in turn, stabilized by means of a copolymer or surfactant that will prevent flocculation or coalescence of the drops. This type of nanoemulsions is determined by its droplet size and distribution, as well as being nanometric emulsions, which unlike microemulsions are kinetically but not thermodynamically stable. So, taking into account the average droplet diameter, nanoemulsion is understood to mean those emulsions having a mean droplet diameter between 20-500 nm, with micro or macro-emulsions having an average droplet diameter between 0.5-100 μm. Preferably, based on the average droplet diameter, nanoemulsion is understood to mean those emulsions having a mean droplet diameter of less than 300 nm.

In the present invention, "nanoparticle" is understood to be any type of particle, or group of particles, or components having an average diameter comprised between 1 nm and 500 nm, as well as those components or particles, or group of particles, having an average diameter comprised between 1 nm and 500 nm of the dispersed phase of a colloidal suspension.

In the present invention, "nanostructured compositions" are understood as combinations of materials and/or conjugates that give rise to nanoparticles.

In the present invention, "nanosystem" is understood to be any type of nanoparticle, nanoemulsion, colloidal structure (eg, liposome, nanocapsule, etc.) and/or conjugate of the ligand-drug or ligand-radioisotope type, wherein in aqueous suspension, said nanoparticle or mean droplet diameter of a nanoemulsion, or colloidal or conjugated structure of the ligand-drug or ligand-radioisotope type, having an average diameter comprised between 1 nm and 500 nm, preferably less than 300 nm, and optimally around 100 nm.

By "average diameter" is meant the hydrodynamic diameter of the particles that diffuse at the same speed. This average particle size is calculated using the Dynamic Light Diffusion (DLS) technique that measures the Brownian motion of nanoparticles and relates it to their size, based on the fact that smaller particles diffuse faster than large particles when the laser strikes about them.

In the present invention, "functionalization" is understood as the union by means of chemical interactions (eg, covalent, electrostatic, hydrophobic, etc.) of molecules that provide functionality to the nanosystems, whether they are drugs for therapeutic use, contrast elements for diagnostic use, ligands. to mediate interactions with molecules/target cells, as well as charged compounds, surfactants or solvents to alter their physicochemical properties (size, dispersion and surface properties).

In the present invention, "sphingomyelin" is understood to mean a lipid of the sphingolipid family, being the most common, found in cell membranes, the only sphingolipid being a phospholipid, having the following chemical structure:

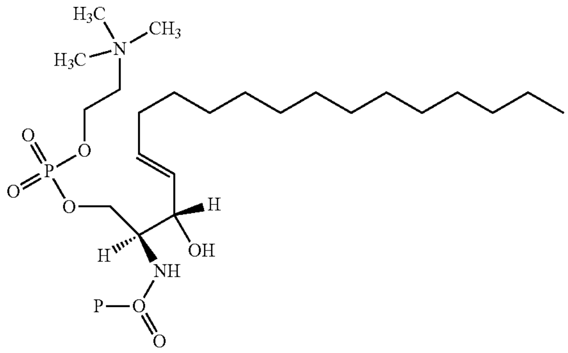

In the present invention "sphingolipid" is understood to mean lipids with amphipathic properties that physiologically represent important biological functions and play an important role in the formation of biological membranes, and are generally classified into phosphoesphingolipids and glycosphingolipids.

In the present invention, "oily nucleus" is understood as oil or mixtures of oils, stabilized by surfactants, preferably by sphingolipids, and can also harbor other types of molecules soluble in them or in suspension, such as drugs, fluorophores, radioisotopes, contrast agents, etc.

In the present invention, "ligand" is understood as a molecule disposed towards the surface of the nanosystems, to favour the interaction thereof with target molecules, as receptors expressed at the level of the cell membrane of tumor cells. Depending on their nature, they can be nucleic acids, aptamers, peptides, proteins, hydrophilic or hydrophobic low molecular weight molecules, as well as derivatives thereof to generate amphiphilic molecules.

In the present invention, "TAS1R3 receptor" is understood as a transmembrane receptor coupled to G protein of taste, which is expressed in taste buds, but also in other tissues such as liver and pancreas, and in tumor cells. There are multiple references to this receiver such as; HGNC: 15661; Entrez Gene: 83756; Ensembl: ENSG00000169962; OMIM: 605865; o UniProtKB: Q7RTX0.

In the present invention, a ligand for the TAS1R3 receptor is understood to be molecules capable of interacting with the TAS1R3 receptor, such as mono and disaccharides, artificial sweeteners such as sucralose, cyclamate, neoesperidine, dihydrochalcone, sweetness inhibitors such as lactisole, proteins such as brazzein, and others specifically designed by means of selection systems such as antibodies, fragments of antibodies, peptides, aptamers, small molecules, proteins, etc.

In the present invention, "conjugates with ligands" means chemical conjugates that incorporate a lysate and a molecule with therapeutic activity (drug, radiopharmaceutical, etc.), or for diagnostic purposes (radioisotope, chelator, gadolinium, etc.).

In the present invention, the "ratio (w/w) oil/sphingolipid" is between 0.005 and 1:10, meaning mass ratio, where the amount of oil is set at 1, and the proportion of sphingolipid is determined in relation to that unit.

DESCRIPTION

In the present invention, the development of formulations for use as a nanotechnological vehicle is illustrated, in particular for the treatment and/or monitoring of localized and/or metastatic tumor disease. Said formulations can be functionalized with ligands capable of interacting or binding to receptors expressed on the cell membrane of tumor cells, and in particular capable of interacting or binding to receptors expressed on the membrane of primary, disseminated or metastatic tumor cells. Also, antitumor drugs or therapeutic biomolecules can be encapsulated in said nanoemulsions and, finally, contrast agents can be incorporated for their use in the in vivo diagnosis in said nanoemulsions.

For this purpose we have developed, using the procedure shown in the examples of the present invention, various nanoemulsions of the oil-in-water type (whose characterization is detailed in the first aspect of the present invention) containing an oil phase or oil core, preferably selected from vitamin E or oleic acid, stabilized by a sphingolipid of the sphingomyelin type, and optionally said nanoemulsion may contain other lipids such as phospholipids, cholesterol, octadecylamine, DOTAP, and pegylated derivatives, as well as conjugates of polyamines with lipid chains. By way of example, the physicochemical properties of said nanoemulsions prepared based on said compounds are shown (Table 1).

TABLE 1

Characterization of nanoemulsions of sphingolipids with different compositions

| COMPOSITION | Ratio (mass) | Size (nm) | PDI | Superficial charge ζ (mv) |
|---|---|---|---|---|
| V:SM | 1:0.005 | 135 ± 1 | 0.1 | −4 ± 6 |
| V:SM | 1:0.01 | 147 ± 8 | 0.1 | −8 ± 7 |
| V:SM | 1:0.1 | 108 ± 2 | 0.1 | −9 ± 6 |
| V:SM | 1:1 | 118 ± 8 | 0.2 | −6 ± 1 |
| V:SM | 1:10 | 201 ± 86 | 0.3 | −9 ± 1 |
| V:SM:DOTAP | 1:0.1:0.1 | 122 ± 2 | 0.1 | +50 ± 2 |
| V:SM:OCT | 1:0.1:0.01 | 95 ± 1 | 0.2 | +58 ± 1 |
| V:SM:CH-DC | 1:0.1:0.01 | 68 ± 1 | 0.3 | +40 ± 6 |
| V:SM:P | 1:0.1:0.1 | 92 ± 31 | 0.3 | +43 ± 7 |
| O:SM | 1:0.1 | 138 ± 1 | 0.1 | −34 ± 1 |
| O:SM | 1:0.2 | 133 ± 2 | 0.2 | −35 ± 1 |
| O:SM | 1:10 | 123 ± 16 | 0.2 | −28 ± 5 |
| O:SM:PC | 1:0.1:0.1 | 145 ± 4 | 0.2 | −35 ± 1 |
| O:SM | 1:0.1 | 86 ± 1 | 0.2 | −30 ± 3 |
| L:SM | 1:0.1 | 184 ± 5 | 0.2 | −27 ± 1 |
| L:SM | 1:0.2 | 169 ± 12 | 0.2 | −25 ± 1 |
| L:SM | 1:0.5 | 171 ± 30 | 0.2 | −32 ± 6 |
| M:SM | 1:0.2 | 55 ± 2 | 0.1 | −23 ± 4 |
| V:Cer | 1:0.1 | 223 ± 4 | 0.2 | −38 ± 5 |
| O:Cer | 1:0.1 | 255 ± 7 | 0.2 | −36 ± 1 |

SM: Sphingomyelin;
V: Vitamin E;
DOTAP: Cationic lipid;
PC: phosphatidylcholine;
OCT: Octadecylamine;
P: Putrescine derivative with an oleic acid chain;
CH-DC: cationic derivative of cholesterol;
O: oleic acid;
L: linoleic acid;
M: Miglyol.
Cer: Ceramide
PDI: Polidispersity Index
ζ: Zeta Potential In addition, we have proceeded to analyze this type of nanoemulsions by transmission electron microscopy, to determine their morphology and size distribution. In FIG. 1 it is possible to see populations of rounded nanoparticles with a homogeneous distribution. It is also noted that the developed nanoemulsions are highly stable, in terms of their colloidal properties, both during storage and in the presence of biological fluids, as shown in FIG. 2.

On the other hand, in order to determine the nanotheranostic value of the nanoemulsions of the present invention, they were functionalized with molecules capable of enhancing their interaction or binding against tumor cells expressing certain receptors of interest such as TAS1R3, guanylyl cyclase C, the leptin receptor, or molecules such as integrins and laminin. These studies were accompanied by the identification of these target receptors/molecules in metastatic tumor cells. In order to carry out said functionalization, the ligands described in Table 2 were acquired and joined by covalent binding to a hydrophobic residue (eg C16, C18 . . . ), with or without a spacer (PEG). In other cases (UROGLys, BRA, INT and LEPT), incubations were performed on preformed nanoemulsions. The sequences of the peptides used (Table 2), and the physicochemical properties of the resulting nanoemulsions are described below (Table 3).

TABLE 2

Description of the ligands used in functionalization studies of nanoemulsions.

| LIGAND | DESCRIPTION |
|---|---|
| LAPI | C18-PEG8-LDFIK |
| UROG | C18-PEG12-NDDCELCVNVACTGCL (SEQ ID NO: 1) Con puentes disulfuro entre la C4-C12 y C7-C15 |
| UROGLys | KKKKKKNDDC(4)ELC(7)VNVAC(12)TGC(15)L (SEQ ID NO: 2) With disulfide bridges between C4-C12 and C7-C15 |
| LACT | Lactisole (N° CAS 150436-68-3)-C16/ Lactisole-C18 |
| BRA | CFYDEKR (SEQ ID NO: 3) |
| LEPT | Recombinant human leptin |
| INT | Human integrin a6 (Phe24-Lys878). MW = 104 KDa Human integrin ß4 (Asn28-Ser710). MW = 84.8 KDa |
| RPM | C18-PEG8-CPIEDRPMC (SEQ ID NO: 4) |

TABLE 3

Composition and physicochemical properties of functionalized nanoemulsions with several ligands of interest.

| LIGAND | COMPOSITION | Size (nm) | PDI | Superficial charge ζ (mv) |
|---|---|---|---|---|
| LAPI | V:SM:LAPI1:0.1:0.01 | 129 ± 3 | 0.1 | +4 ± 1 |
| UROG | O:SM:UROG 1:0.2:0.01 | 135 ± 4 | 0.1 | −24 ± 5 |
| UROGLys | O:SM:UROGLys 1:0.2:0.01 | 148 ± 20 | 0.2 | −34 ± 4 |
| LACT | O:SM:LACT1:0.1:0.1 | 139 ± 8 | 0.2 | −59 ± 4 |
| BRA | O:SM:PC:BRA1:0.1:0.1:0.005 | 161 ± 4 | 0.2 | −33 ± 2 |
| INT | V:SM:INT1:0.1:0.01 | 118 ± 1 | 0.1 | −10 ± 1 |
| LEPT | V:SM:LEPT1:0.1:0.01 | 242 ± 9 | 0.2 | −8 ± 1 |
| RPM | V:SM:RPM1:0.1:0.05 | 126 ± 0.4 | 0.1 | −28 ± 1 |

SM: Sphingomyelin;
V: Vitamin E;
O: oleic acid;
OCT: Octadecylamine;
LAPI: leptin peptide;
UROG: Uroguaniline,
UROGLys: Uroguaniline cationized with lysines;
Lact; lactisole;
BRA: brazzein peptide;
LEP: leptin;
INT: extracellular fraction of an integrin;
RPM: Peptide against an integrin.
PDI: Polydispersity index
ζ: Zeta Potential It is noted that said functionalizations were carried out as described in example 3. To this end, nanoemulsions with different ligand density were optimized, and in all cases their colloidal stability was determined during storage and in the presence of biological means. Furthermore, it is important to mention that the functionalization of the nanosystems described throughout this report containing sphingomyelin with molecules of low molecular weight, as would be the case of lactisole, is very interesting since it is a ligand that is easy to produce and scale, and very cheap in relation to conventional ligands such as antibodies, peptides and proteins. This type of formulations also presents a high interest because it is directed to the TAS1R3 receptor which has a series of advantages that are described throughout the patent memory.

Having seen the possibility of functionalizing the nanosystems of the invention, several types of molecules with therapeutic activity were associated with the nanoemulsions of the invention, both to determine their physicochemical properties and their potential activity. Some examples of nanoemulsions loaded with these molecules, and their characterization, are shown in the following table (Table 4). Said examples together with the information provided in the examples of the present invention demonstrate the therapeutic potential of the nanoemulsions of the present invention.

TABLE 4

Composition and physicochemical properties of functionalized nanoemulsions with several therapeutic molecules.

| COMPOSITION | Therapeutic molecule | Size (nm) | PDI | Superficial charge ζ (mv) | Association Efficacy (%) |
|---|---|---|---|---|---|
| V:SM 1:0.1 | miRNA | 110 ± 6 | 0.1 | −9 ± 1 | 15 ± 1 |
| V:SM 1:0.1 | Docetaxel | 120 ± 3 | 0.1 | −19 ± 4 | 24 ± 6 |
| L:SM 1:0.2 | Paclitaxel | 157 ± 5 | 0.1 | −3 ± 1 | 18 ± 5 |
| V:SM 1:0.1 | Curcumina | 121 ± 2 | 0.1 | −21 ± 2 | 98 ± 1 |
| V:SM:OCT 1:0.1:0.01 | miRNA | 150 ± 3 | 0.1 | −16 ± 6 | >90% |
| V:SM:DOTAP 1:0.1:0.1 | mRNA | 190 ± 6 | 0.2 | +27 ± 2 | >90% |
| V:SM:DOTA 1:0.1:0.1 | pDNA | 172 ± 5 | 0.1 | −8 ± 1 | >90% |
| V:SM:P 1:0.1:0.1 | pDNA | 167 ± 17 | 0.2 | +33 ± 4 | >90% |

SM: Sphingomyelin;
V: Vitamin E;
L: linoleic acid;
O: oleic acid;
OCT: Octadecylamine;
DOTAP: Cationic lipid;
P: Putrescine derivative with an oleic acid chain;
miRNA: microRNA;
mRNA: messenger RNA;
pDNA: plasmid DNA.
PDI: Polydispersity index
ζ: Zeta potential Apart from associating several types of molecules with therapeutic activity and with the aim of developing nanotheranostics, we associate several elements that allow the visualization/tracking of nanoemulsions, using optical imaging (IVIS) and molecular systems (PET/SPECT/MRI). Table 5 shows the elements that we use, demonstrating that the nanoemulsions of the present invention have a potential diagnostic value.

TABLE 5

Imaging elements that have been associated with nanoemulsions Particle/Molecule

| Magnetic Nanoparticles (SPIONs) | Chelating agents | Radioisotopes | Fluorescent Markers |
|---|---|---|---|
| Magnetic nanoparticles coated with oleic acid | DTPA-PE | 68Ga, 18F | DiD, DiR, Nile Red, ICG, Alexa Fluor, Cy3, Cy5, Cy7 |

TABLE 6

Composition and physicochemical properties of functionalized nanoemulsions with several contrast agents.

| COMPOSITION | Contrast Agents | Size (nm) | PDI | Superficial Charge ζ (mv) |
|---|---|---|---|---|
| O:SM:LACT 1:0.1:0.1 | — | 139 ± 8 | 0.2 | −59 ± 4 |
| | DTPA | 146 ± 9 | 0.2 | −59 ± 6 |
| | SPIONs | 275 ± 12 | 0.1 | −57 ± 1 |
| | DTPA-PE + SPIONs | 265 ± 19 | 0.1 | −61 ± 3 |

SM: Sphingomyelin;
O: oleic acid;
LACT: Lactisole;
DTPA-PE: chelating agent;
SPIONs: superparamagnetic nanoparticles.
PDI: Polydispersity index
ζ: Zeta potential In addition to the foregoing, the toxicity of the nanoemulsions of the present invention was studied in cell culture and mice (FIG. 3). It was observed that they hardly induce toxicity in cell cultures (A). The toxicity is not altered by incorporating a ligand to the surface of the nanoemulsions, and by way of example the toxicity of nanoemulsions is presented without functionalizing and functionalized with the ligand lactisole (B). There was also no increase in deaths compared to control (water) in tests on zebrafish embryos, after 96 h of incubation. And more importantly, no apparent toxicity is observed after several consecutive intravenous injections of nanoemulsions at concentrations of 10 and 20 mg/mL in healthy mice (C). Therefore, it is verified that the nanoemulsions of the present invention show low toxicity since the major components are natural lipids.

On the other hand, and in order to determine the effectiveness of the nanoemulsions of the invention, in particular of sphingomyelin nanoemulsions, the internalization of said nanoemulsions in tumor cells of different origin was evaluated. In this regard, it was determined that, in general, the sphingomyelin nanoemulsions of the invention have a great capacity to be internalized (FIG. 4). We were able to observe by confocal microscopy that V:SM 1:0.1 formulations loaded with the Nile Red fluorophore gave rise to an intense red signal around the nuclei of cells counter-stained with DAPI, regardless of the origin thereof (eg, colon, lung), prostate and pancreas) (A). In addition, the internalization efficiency is variable and can be controlled by the composition, since for example the cationic nanoemulsions V:SM: DOTAP (1:0.1:0.1) were internalized more effectively in colon cells when compared with nanoemulsions neutral V:SM (B). It was verified that indeed the signal corresponding to the nanoemulsions was in the cell cytoplasm, marked with green since transformed tumor cells were used to express green protein (GFP); co-localization of the marker corresponding to the nanoemulsions and the green of the cellular cytoplasm (C) is observed. This effective internalization gives rise to the effective intracellular release of the associated therapeutic molecules (FIG. 5). By using, for example, nucleic acids labeled with a fluorophore, Cy5, it was possible to observe how nanoemulsions are capable of transporting it to the cellular cytoplasm, since in this case the signal in the cellular cytoplasm of tumor cells transformed with GFP corresponds to the labeled RNA (A). In the case of nanoemulsions incorporating magnetic nanoparticles, it is possible to observe, by means of transmission electron microscopy, the contrast thereof in vacuoles of cells incubated with this formulation (B).

On the other hand, we have observed a greater internalization in the case of functionalized nanoemulsions. This is true, for example, in the case of O:SM 1:0.1 nanoemulsions marked with Nile Red and functionalized with LAPI, where the number of cells positive for Nile Red was higher in the case of this formulation when compared with respect to the control without ligand (a greater displacement of the curve and a higher average intensity is observed) (FIG. 6). This fact is repeated in the case of O:SM 1:0.1 nanoemulsions functionalized with lactisole (FIG. 7). First, the DiD signal encapsulated in the nanoemulsions is greater for the functionalized nanoemulsions (O:SM:Lact 1:0.1:0.1) (lower picture), which confirms that the degree of internalization is greater than in the case of control nanoemulsions (O:SM 1:0.1) (A). In addition, it has been observed that when tumor cells express the target receptor with less intensity (in this case TAS1R3 in SVV620 cells cultured under normal conditions (low expression) or with low glucose content (high expression)), the intensity of the signal (B).

In addition, the efficacy of the sphingomyelin nanoemulsions of the invention in cell cultures was evaluated (FIG. 9). Cytotoxicity assays reveal that nanoemulsions (O:SM 1:0.1) can efficiently release antitumor drugs and lead to a decrease in cell viability (in this case etoposide), a more pronounced effect in the case of functionalized nanoemulsions with a ligand (in this case lactisole O:SM:Lact 1:0.1:0.1) (A). This is also confirmed for the case of targeted therapies, such as gene therapy. Nanoemulsions V:SM:DOTAP 1:0.1:0.1 and V:SM:P 1:0.1:0.1 are capable of efficiently transfecting tumor cells with plasmid that encodes a red protein (mCherry), observing signal in the cellular cytoplasm (B) In the case of plasmids that encode an IncRNA, a significant increase in its expression (TG1) was observed, quantified by RT-PCR (C). In the case of siRNA, using one that decreases the expression of luciferase in transformed cells, a reduction in the expression of this protein (VDOTAP-CL3) is observed, comparable to the reduction that can be obtained with the commercial reference vector, lipofectamine (D). The efficacy of sphingomyelin nanoemulsions was also evaluated in animal models (animals xenotransplanted with tumor cells of colon cancer, SVV620) (FIG. 9), After administering the nanoemulsions intravenously (O:SM: UROG 1:0.1:0.01) a lower tumor growth is observed, in relation to the control (animals that received injections of saline solution).

Based on all the results discussed above, the potential of nanoemulsions of the oil-in-water type comprising an oil core and stabilized by a sphingolipid, preferably of the sphingomyelin type, is demonstrated for use as a nanotechnological vehicle, in particular for the management of disease tumor in early stages and more particularly when it comes to metastatic disease. In this sense, the present invention demonstrates that the functionalization of said vehicle with ligands against receptors expressed in the cell membrane of tumor cells, in particular in the membrane of dismeminated and metastatic tumor cells, makes it a unit with a strong therapeutic potential useful both for the encapsulation of antitumor drugs in said vehicle and for the incorporation of a contrast agent for use in in vivo diagnosis.

Thus, a first aspect of the invention relates to a nanoemulsion (hereinafter "nanoemulsion of the present invention") of the oil-in-water (o/w) type, comprising:

An aqueous phase;

An oil phase or oil core comprising an oil; and

A sphingolipid selected from the list consisting of sphingomyelin, ceramide, sphingosine, ganglioside, globose, psychosine and cerebroside;

where the ratio (p/p) sphingolipid/oil is between 0.005 and 10.

In a preferred embodiment of the first aspect of the invention, the sphingolipid is sphingomyelin.

In another preferred embodiment of the first aspect of the invention, the concentration of the sphingolipid, preferably of the sphingomyelin type, is at a concentration of between 1% and 6% by weight on the total volume of the nanoemulsion (w/v).

In another preferred embodiment of the first aspect of the invention, the oil of the oil phase or oil core is selected from the list consisting of a tocopherol (vitamin E), sunflower oil, peanut, avocado, argan, almond, calendula, coconut, wheat germ, arnica, borage, sesame, cotton, olive (oleic acid), castor bean, soybean, safflower, palm, wheat germ, tea tree, jojoba, linseed, silicone, glycerol, triglyceride oils, hypericum, rose mosqueta, isopropyl myristate, tributyrin, squalene, or any combination thereof.

Preferably, the oil phase consists of α-tocopherol (vitamin E), oleic acid, linoleic acid and/or triglycerides.

In another preferred embodiment of the first aspect of the invention, said nanoemulsion further comprises other membrane lipids (phospholipid, sterols and glycolipids), and/or a cationic lipid such as DOTAP or octadecylamine, and/or a polyamine or derivatives, as well as derivatives thereof with polyethylene glycol.

In another preferred embodiment of the first aspect of the invention, said nanoemulsion is functionalized with at least one of the following elements:

Therapeutic molecules; or

Contrast elements.

Where the therapeutic molecules are preferably selected from the list consisting of:

Drugs, preferably antitumor drugs such as carmofur, etoposide docetaxel, paclitaxel, gemcitabine, or derivatives thereof;

Nucleic acids;

Peptides;

Proteins;

Antibodies or fragments thereof;

Aptamers

Small organic molecules;

Lipids with antitumor activity such as edelfosine;

Compounds of natural origin with antitumor properties such as curcumin or resveratrol;

as well as any combination of them; and

Where the contrast elements are preferably selected from the list consisting of:

Fluorophores such as green indiancyanine (ICG), 1,1-dioctadecyl-3,3,3,3-tetramethylindotricarbocyanine iodide (DiR), 1,1-dioctadecyl-3,3,3,3-tetramethylindodicarbocyanine perchlorate (DiD), nile Red or Alexa Fluor;

Inorganic nanoparticles such as superparamagnetic iron oxide particles (SPIONs);

Chelating agents such as 1,4,7,10-Tetraazacyclododecane-1,4,7,10-tetraacetic acid (DOTA) or 1,2-distearoyl-sn-glycero-3-phosphoethanolamine-N-diethylenetriamine-pentaacetic acid (DTPA-PE) or 1,4,7-Triazacyclononane-1,4,7-triacetic acid (NOTE) or NOTE modified with a lipid for the complexation of gadolinium, or radioisotopes such as Gallium or Indium;

Other radioisotopes such as fluorine (18F), gallium (68Ga), iodine (125I), Indium (111In), and derivatives.

Perfluorocarbons such as perfluorohexane and octafluoropropane;

as well as any combination of them.

On the other hand, the authors of the present invention have identified in CTCs (circulating tumor cells) and in both primary and disseminated or metastatic tumors, a new receptor, specifically the Tas1R3 receptor (it is a taste receptor). The expression of said receptor varies depending on the presence of glucose, and the line and location of it (more metastatic higher expression).

Due to the enormous potential of this receptor for the selective direction of molecules, such as nanoparticles, and taking into account that we know of the existence of molecules that interact with this receptor, and are not endogenous, and therefore do not occur competition phenomena; we have selected several ligands of the receptor, in particular several sweeteners, to validate the hypothesis that by functionalizing the nanosystems of the present invention with said ligands, we will be able to direct said nanosystems against tumors, such as primary tumors or disseminated tumor cells as CTCs (tumor cells) circulating) and metastatic cells (see examples and figures).

Once the nanoemulsions have been functionalized, we have observed that these functionalized nanoparticles accumulate more efficiently in cells that express the receptor (FIGS. 6-11)

Thus, in another preferred embodiment of the first aspect of the invention, the nanoemulsion of the present invention is functionalized with ligands such as small molecules, whether or not linked to a carbon chain, proteins, peptides or aptamers, suitable for cellular vehiculization. Preferably, said nanoemulsion of the present invention is functionalized with ligands against tumor cells expressing certain receptors of interest such as TAS1R3, guanylyl cyclase C, the leptin receptor, or molecules such as integrins and laminin. In particular, said ligands are selected from the list consisting of the peptide lactisole or brazzein. More preferably, said nanoemulsion of the present invention is functionalized with ligands against the guanylyl cyclase, leptin, or TAS1R3 receptor, with ligands selected from the list consisting of peptides; proteins or fragments, antibodies or fragments thereof, aptamers, organic molecules of small size, molecules described as capable of interacting with them, or derivatives.

In yet another preferred embodiment of the first aspect of the invention, the nanoemulsion of the present invention is functionalized with uroguaniline, uroguanylin catalyzed with lysines, with the extracellular fraction of an integrin INT or with RPM (peptide sequence of the RPM peptide: CPIEDRPMC) (SEQ ID NO: 5).

In yet another preferred embodiment of the first aspect of the invention, the nanoemulsion of the present invention is doubly functionalized with ligands suitable for cellular vehiculization and at least one therapeutic molecule or contrast element, as defined above.

A second aspect of the invention relates to a process for obtaining the nanoemulsion of the present invention, comprising: i) dissolving the oils and/or the sphingolipids in ethanol preferably, or if necessary in other miscible organic solvents with water, or mixtures; ii) adding this phase on the aqueous phase, water, saline solutions, buffered solutions, or sugar solutions, under gentle magnetic stirring, or optionally homogenizing or applying ultrasound; iii) optionally, adding a compound, contrast agent, therapeutic molecule or ligand in one of the two previous phases, depending on the compound with which we wanted to functionalize the nanoemulsion and its solubility properties; iv) alternatively, microfluidic systems can be used for the mixing of the components; v) nanoemulsions can also be prepared using different physical methods for mixing both phases, such as by homogenization or sonication; vi) nanoemulsions can be functionalized by adding all the components at the time of preparation, or incorporating different elements on preformed nanoemulsions, through chemical reactions or physical processes.

A third aspect of the invention relates to the nanoemulsion of the present invention, for use in therapy. In particular, for use in the treatment of cancer, in particular of breast cancer, melanoma, uveal melanoma, pancreatic cancer, lung cancer, prostate cancer, stomach cancer, head and neck cancer, sarcoma, glioblastoma, neuroblastoma, cancer of the colon and rectum, cancer of the head and neck, kidney and bladder cancer, and hepatocarcinoma. More particularly, for its use in the treatment of cancer metastasis. More particularly, for its use in in vivo diagnosis.

A fourth aspect of the invention relates to a pharmaceutical composition comprising the nanoemulsion of the present invention, and one or more pharmaceutically acceptable excipients.

Finally, as already mentioned, the authors of the present invention have identified in CTCs (circulating tumor cells) and in tumors, a new receptor, in particular the Tas1R3 receptor (see example 6). Furthermore, in the present invention it is demonstrated (see FIG. 7) that once the nanoemulsions of the present invention are functionalized with ligands to this receptor, an intracellular accumulation of said nanoemulsions is observed more efficiently in cells expressing the receptor, i.e., in tumor cells (see example 7).

Thus, a fifth aspect of the invention relates to a compound of the group selected from the list consisting of antibodies, antibody fragments, aptamers or peptides capable of binding to the TAS1R3 receptor, for use in the functionalization of nanosystems or conjugates in front of tumor cells. Preferably, against primary, disseminated or circulating tumor cells.

In a preferred embodiment of the fifth aspect of the invention, said compound is selected from the list consisting of the peptide derived from leptin or bracein, preferably bracein.

In a particularly preferred embodiment, the present invention refers to oil in water (o/w) nanoemulsion, comprising: a) An aqueous phase; b) An oily nucleus consisting of α-tocopherol (that is to say that the oil of the oily nucleous consist of α-tocopherol); and c) sphingomyelin (as a stabilizer or surfactant).

This specific combination (i.e. the combination of an aqueous phase, an oily nucleus consisting of α-tocopherol, and sphingomyelin) confers to the present invention the opportunity of obtaining versatile nanoemulsions to be used both with therapeutic and diagnosis purposes, having a reduced toxicity and also a high stability during storage in saline and plasma media.

Regarding the toxicity of the nanoemulsions of the invention, the present invention already explained that the toxicity of the nanoemulsions of the present invention was studied in cell culture and mice (FIG. 3). In this FIG. 3 the cell viability assay (MTT) of nanoemulsions with different compositions VSM (vitamin E and sphingomyelin 1:0.1) is performed. It was observed that they hardly induce toxicity in cell cultures (FIG. 3A). The toxicity is not altered by incorporating a ligand to the surface of the nanoemulsions, and by way of example the toxicity of nanoemulsions is presented without functionalizing and functionalized with the ligand lactisole (FIG. 3B). There was also no increase in deaths compared to control (water) in tests on zebrafish embryos, after 96 h of incubation. More important, no apparent toxicity is observed after several consecutive intravenous injections of nanoemulsions at concentrations of 10 and 20 mg/mL in healthy mice (FIG. 3C). Therefore, it is verified that the nanoemulsions of the present invention show low toxicity since the major components are natural and neutral lipids. Moreover, please refer to FIG. 13 showing a comparative assay wherein nanoemulsions comprising vitamin E+sphingomyelin (VSM) are compared with nanoemulsions comprising vitamin E+ceramide (VCer6). Such as it can be seen in FIG. 13 the toxicity of the nanoemulsions comprising ceramide is significantly higher.

This is an indication that not all the sphingolipids are equally suitable for obtaining non-toxic theranostic nanoemulsions, because, in fact, nanoemulsions comprising ceramide are clearly toxic and therefore not appropriate or advisable for diagnosis purposes. So, in the present invention, the sphingolipid sphingomyelin was particularly elected for obtaining theranostic nanoemulsions due to its reduced toxicity.

In addition, as shown in FIG. 14, not all the oily nucleus are equally suitable for obtaining non-toxic theranostic nanoemulsions. As shown in FIG. 14, the combination of sphingomyelin with linoleic acid (L) or with oleic acid (O) demonstrates that the use of oily nucleus such as linoleic acid (L) or oleic acid (O) is highly toxic. Such toxicity is significantly reduced when vitamin E is used.

Regarding the stability, it is important to note that the nanoemulsions of the invention are highly stable, in terms of their colloidal properties, both during storage and in the presence of biological fluids, as shown in FIG. 2 of the application as filed that deals with the stability of nanoemulsions based on sphingomyelin and vitamin E. In fact, such as it can be seen in FIG. 15, the nanoemulsion comprising sphingomyelin are more stable both during storage and in saline and plasma media, as compared with the nanoemulsions comprising other sphingolipids like ceramide, or a phospholipid like phosphatidylcholine.

Moreover, the inventors of the present invention have carried out comparative tests showing the stability of different nanoemulsions all of them comprising sphingomyelin and different oily nucleuses (see FIG. 16). Interestingly, the stability of those nanoemulsions comprising a linoleic or oleic acid nucleus is clearly diminished in comparison to the stability shown when vitamin E is used.

In addition, and as illustrated in FIG. 17, under stress conditions at 40° C. and 75% humidity (conditions required or mandatory for regulatory approval), those nanoemulsions having an oleic acid nucleus (OSM) or a different oily nucleous (Migliol) and surfactant (phosphatidylcholine) are clearly inestable, whereas those nanoemulsions comprising vitamin E and sphingomyelin are stable.

The above data indicate that not all the lipids or sphingolipids are equally suitable for obtaining stable and non-toxic nanoemulsions. Therefore, in the present invention, the combination of the sphingolipid sphingomyelin and the oily nucleus vitamin E was particularly elected for obtaining non-toxic nanoemulsions with a high stability during storage, in saline, and plasma media.

The following examples serve a merely illustrative function of the invention but in no case limiting thereof.

EXAMPLES

Example 1. Preparation of the Nanoemulsions of the Invention

The preparation of the nanoparticles was carried out by means of the ethanol injection technique, for which a stock was prepared with the oil: surfactant ratio (sphingolipids in combination or not with other surfactants), necessary in each case (Organic phase, FO), and injected 100 μL (using a syringe of 0.5 mL insulin Myjector, U-100 Insulin, Terumo) on 900 μL of H2O (aqueous phase, FA) contained in a small vial of 2 mL, and under magnetic stirring. The formation of oil-in-water (O/W) nanoemulsions occurred spontaneously under these conditions, presenting a spherical morphology and giving places to homogenous populations (FIG. 1). The structure consists of an oil core stabilized by sphingomyelin and sometimes other lipids, and are in principle suitable systems for the encapsulation in the nucleus of hydrophobic molecules, being able to associate also another type of amphiphilic or hydrophilic molecules, which will be arranged preferably in the interface or will be associated on the surface of the nanoemulsions.

For the characterization of the formulations, a Zetasizer® (NanoZS Malvern Instruments, England) was used, which allows to determine the particle size and polydispersity index (PdI) by dynamic light scattering (DLS), as well as its potential (Z), by Doppler laser anemia (LDA). All samples are analyzed after dilution with MilliQ water, at room temperature, and with a detection angle of 90°. Each sample is given 3 measurements and the average is provided. This type of measurements is also used to determine the colloidal stability of the formulations, either during storage, or after incubation in more complex media, as shown in FIG. 2.

Example 2. Optimization of HPLC Methods

High performance liquid chromatography (HPLC) was used to determine the association to the developed nanostructures, both of the associated ligands, and of the therapeutic molecules of interest.

For the optimization of the methods, the characteristics of each molecule were taken into account. As for the ligands, the compounds described in Table 2 are contemplated, which after their incorporation into the formulation, give rise to functionalized nanoemulsions as those shown in Table 3. In the case of the peptides, the analysis was carried out at 220 nm, with a combination of water and acetonitrile as the mobile phase, usually less than 60% acetonitrile being sufficient for elution. It was also important to add in the mobile phase a small percentage of TFA (0.2%), an ion-pairing agent, highly used at its high volatility (Agilent, 2013), which allows the separation of ionic substances on phase HPLC columns. reverse by controlling retention and selectivity. Also in the case of some amphiphilic molecules, as is the case of the lactisole derivative, a small percentage of TFA (0.05%) was added, since it has a structure similar to a fatty acid and provides the help already mentioned. In some cases, it was also necessary to adjust the appropriate wavelength for the analysis, performing UV-Vis scans with a UV/Vis DU-730 spectrophotometer (Beckman Coulter).

Likewise, the characterization of nanoemulsions loaded with drugs, such as those listed in Table 4, such as docetaxel and paclitaxel, was performed by HPLC, in order to analyze the encapsulation efficiency of the compound of interest. To do this, they took into account the characteristics of each of them, such as hydrophobicity (Log P), since, more hydrophilic compounds elute with a more polar mobile phase (more water) while more hydrophobic compounds they need a more apolar mobile phase for their elution. Other parameters that were adjusted were the temperature and the injection volume. In the case of temperature, it allows to accelerate or delay the exit of the peak: If the peak appears too close to the front of the solvent, the column can be cooled and thus delay the elution; whereas, if the peak appears at long times, giving rise to slow chromatograms and analyzes, the temperature can be increased to accelerate the exit of the compound through the column. In the case of the injection volume, this allows to increase the height of the peak and therefore improve the limit of detection (LOD) and the limit of quantification (LOQ). Once the method is optimized, it is important to make sure that there is no interaction with the nanoparticle components, so that the chromatogram is altered. In all cases we used an HPLC system (1260 Infinity II, Agilent) equipped with a G7111A pump, a G7129A autosampler and a G7114A UV-Vis detector, with an InfinityLab Poroshell 120EC-C18 column (Agilent, 4.6×100 mm, 4 μm pore size).

In the case of nucleic acids, the analysis to determine the association efficiency was carried out by agarose gel electrophoresis.

Example 3. Functionalization of the Nanosystems

The developed nanosystems were functionalized with the ligands mentioned in table 3. The characterization of said developed nanosystems was performed in terms of size, dispersion, and surface charge, in the same way as in the case of nanoemulsions without functionalization (example 1). Next, the procedure followed is grouped by the type of preparation in four cases.

3.1. Functionalization with Lipid Conjugates of Peptides, LAPI, UROG y RPM (V:SM:LAPI 1:0,1:0,01, O:SM:UROG 1:0,2:0,01, y V:SM:RPM 1:0,1:0,05).

The association of this ligand to nanoemulsions was made by adding 50 μL of a stock of each of the derivatives after dissolution in ethanol (at a concentration of 1 mg/ml in the case of LAPI and UROG, or 0.5 mg/ml for RPM, to the organic phase, which was then injected with 1 ml of water under stirring, to obtain the functionalized nanoemulsions.

3.2. Functionalization with the Hydrophilic Peptides (Cationic Peptide derived from Uroquaniline O:SM:UROGLys 1:0,2:0,01, and with the Peptide derived from Brazzein O:SM:PC:BRA 1:0,1:0,1:0,005).

To carry out the functionalization with both peptides, we started with the preformed white formulations (O:SM 1:0.2 and O:SM:PC 1:0.1:0.1). Over 100 μL of these magnetic stirring nanoemulsions, 200 rpm, another 100 μL of aqueous peptide solution was added gradually, by drip. Once the addition was complete, the agitation was maintained for 20 minutes to favour the adsorption of the peptide on the surface of the preformed nanoemulsions. Different concentrations of peptides were tested, which were characterized as described in Example 1, and their colloidal stability was determined at 24 h.

3.3. Functionalization with a Lipid Conjugate of the Lactisole Ligand (O:SM:LACT 1:0,1:0,1).

The association of this ligand (lactisole covalently linked to a C16-C18 chain) to the nanoemulsions was done by adding 50 μL of a stock of 10 mg/ml to the organic phase (O:LM 1:0.1, in 50 μl of ethanol) which, Then, Milli-Q (MilliporeMilli-Q® system) was injected with 1 ml of Milli-Q water under magnetic stirring, to obtain the functionalized nanoemulsion.

3.4. Functionalization with Proteins (Integrin V:SM:INT 1:0,1:0,01, and Leptin V:SM:LEPT 1:0,1:0,01).

To carry out the functionalization with both proteins, we started with the white formulations (V:LM, 1:0.1). In the first case, over 50 μL of preformed nanoemulsions in magnetic stirring, 25 μL of the integrin solution was added, and in the second, the volumes were 100 μL and 50 μL for the preformed nanoemulsions and leptin respectively.

The results associated with the cellular internalization of nanoemulsions functionalized with a derivative of LAPI, lactisole, and RPM, are shown in FIGS. 6, 7, 8, and 18, where a strong accumulation of nanosystems can be seen in tumor cells expressing the receptor against which the nanoemulsion has been functionalized.

Example 4. Association of Contrast Molecules to Functionalized Particles

The encapsulation of hydrophobic superparamagnetic nanoparticles (SPIONs) coated with oleic acid in the nanoemulsions was carried out with the method described in Example 1 with minor modifications. 15 μL of SPIONs dissolved in chloroform at a concentration of 80 mg/mL were added to the organic phase, which was sonicated for 5 minutes in an ice bath before injection in water for the preparation of the nanoemulsions with and without the ligand. The suspension was stirred for 10 minutes on an orbital shaker. Finally, they were characterized according to their size, PdI and zeta potential. DTPA-PE was also added for the subsequent marking of nanoemulsions with 68Ga, and visualization by PET. In this case, DTPA-PE, previously dissolved in ethanol at a concentration of 20 mg/mL, was incorporated into the organic phase, together with the lipids (1.25 μL, 2.5 μL or 5 μL), before being produced. the injection of this organic phase into the aqueous medium, resulting in the formation of the nanoemulsions.

The results derived from this type of association are shown in Table 6 and FIG. 5, which shows images of cells that have endocycled said nanoemulsions incorporating SPIONs.

Example 5. Encapsulation of Drugs

In the present experimental work, the therapeutic molecules of Table 4 were encapsulated. For the encapsulation of the hydrophobic molecules, solutions of them were prepared in organic solvents, preferably ethanol, and a small volume was incorporated in the organic phase, together with the lipids, previous preparation of the nanoemulsions. For example, in the case of paclitaxel, a solution of 40 mg/mL in DMSO was prepared, and 1.25 μL in the organic phase (100 μL of lipids in ethanol) was added. The characteristics of the formulation are detailed in Table 4. HPLC was used to determine the concentration of drug in the colloidal suspension (example 2).

As for the association of nucleic acids, they were associated with preformed nanoemulsions. For example, in the case of putrescine nanoemulsions (V:SM:P 1:0.1:0.1), described in Table 4, 100 μL of a solution of pmCherry (5 μg) on 100 μL of the nanoemulsion, under magnetic stirring. After 20 min of incubation, the nanoemulsions were characterized. By means of an agarose electrophoresis gel, the absence of a migration band corresponding to the pDNA previously associated with the nanoemulsions was observed, thus confirming the effectiveness of the association. Taking into account the limit of detection of the technique, we can conclude that the efficiency is greater than 90%.

Example 6. Expression of Biomarkers in Tumor Cells

The expression of several biomarkers of interest was analyzed for the functionalization and selective direction of nanoemulsions to tumor cells (FIG. 12). On the one hand, an expression analysis of TAS1R3 was performed on samples of tumor tissue and healthy paraffin. To do this, we performed RNA extraction from 5 paraffin sections of 14 microns each using a specific extraction kit for paraffinized samples (RNeasy FFPE kit, QIAGEN). In order to know the concentration of it, the Nanodrop equipment (Nanodrop 2000C, Thermoscientific) was used. With these data, the normalization of the RNA concentration in each sample was carried out, placing a total of 2 μg, in a final volume of 10 μl with nuclease-free water. Next, the High Capacity cDNA Reverse Transcription Kit (Appliesbiosystems) was used and a thermal cycler (peq STAR 96HPL, VWR®) was used for the passage of RNA to cDNA. Once the cDNA was obtained, the mixture was carried out with the probe specific for Tas1R3 together with the Taqman Universal PCR MasterMix. GAPDH was used as control or housekeeping, and the polymerase chain reaction was carried out in StepOne Plus-Real-Time PCR system, AppliedBiosystems®.

As regards the evaluation of expression in cell cultures, several types of cell lines were used, obtained from ATCC (American Type Culture Collection). Metastatic colon cells from the lymph node (SW620, CCL-227), colorectal adenocarcinoma epithelial cells (SW480, CCL-228 and HT-29, HTB-38), lung carcinoma epithelial cells (A549. 185), liver metastatic lung cells (H1755, CRL-5892), pancreatic carcinoma cells (MIA PaCa-2, CRL-1420), and glioblastoma cells (U118, HTB-15, and U87MG, HTB-14).). The SW620, SW480, A549, U118 and U87MG lines were maintained in DMEM HG medium (Dulbecco'sModifiedEagle'sMedium—High glucose, Sigma-Aldrich), and the H1755 line in RPMI 1640 medium (Gibco®, LifeTecnologies), both supplemented to the 10% with fetal bovine serum (Gibco®, LifeTecnologies) and 1% with antibiotic (penicillin and streptomycin, Sigma-Aldrich). All were tested for mycoplasma.

For the quantitative analysis of the expression of TAS1R3, a polymerase chain reaction was carried out with reverse transcriptase (RT-PCR), starting from RNA extracted from all cell lines in culture. First, the cells were routinely trypsinized, and then counting them using the Neubauer chamber and thus being able to isolate 5 million cells from each line to start from a comparable cell number. RNA extraction was carried out using the extraction kit (GeneJET RNA Purification Kit, ThermoScientic), and the analysis was carried out in a manner similar to that described in a previous paragraph. Once the procedure was finished, the data was analyzed. Cell lines of colorectal cancer of metastatic origin, isolated from lymph node (SW620), are those that show a greater expression of it.

As for the immunofluorescence studies, the cells were seeded one day before the test was performed in 8-well μ-chamber (PLC30108, SPL LifeSciences) or in coverslips. After 24 hours, the culture medium was removed by aspiration and washed with PBS 1×, to proceed to fix the cells with 4% paraformaldehyde, for 15 minutes at room temperature. They were washed with PBS 1× twice, and then the cells were permeabilized with 0.2% triton 100×, for 10 minutes at room temperature. After washing the triton, the cells were incubated with primary and secondary antibodies, as described in the following table.

| BIO-MARKER | Primary Antibody | Incubation conditions | Secondary Antibody | Incubation conditions |
|---|---|---|---|---|
| TAS1R3 | Polyclonal Rabbit Abcam ab65419 | 1:50 (1 hour, RT) | Alexa Fluor 488 anti-conejo. Jackson Immunoresearch. 115-545-144 | 1:500 (1 hour, RT) |
| GCC | Polyclonal Rabbit Abcam ab107755 | 1:50 (1 hour, RT) | Alexa Fluor 488 anti-conejo. Jackson Immunoresearch. 115-545-144 | 1:500 (1 hour, RT) |
| Leptin Receptor | Monoclonal mouse [LPR-02] Abcam ab2143 | 1:50 (1 hour, RT) | Alexa Fluor 488 anti-ratón. Jackson Immunoresearch. 115-545-003 | 1:500 (1 hour, RT) |
| Laminin-5 | Monoclonal mouse, Dako [M7262] | 1:50 (1 hour, RT) | Alexa Fluor 488 anti-ratón. Jackson Immunoresearch. 115-545-003 | 1:500 (1 hour, RT) |

Hoechst 33342 (ThermoFisher®) (1:1000 dilution) was subsequently added, and incubated for one hour, protecting the fluorophore from possible light degradation. Once the incubation time had passed, it was washed again with PBS1× three times in agitation, to then remove the walls of the μ-chamber, apply the Mowiol mounting medium (Calbiochem) and place the coverslip on the sample. It was left overnight to dry at room temperature protected from the dark, and the next day it was stored at −20° C. until its observation in the confocal microscope (Confocal Leica Laser Microscope SP8®).

Example 7. Studies of Interaction of Nanoemulsions with Tumor Cells and Intracellular Release of Associated Molecules To study the interaction of nanoemulsions with tumor cells, fluorescent nanoemulsions were prepared by adding a small amount of fluorochrome (Nile Red, DiD or DiR), dissolved in ethanol, to the organic phase after the formation of nanoemulsions. The percentage of fluorochrome, by weight, was set between 0.001 and 0.5%. For example, an association efficiency between 85-95% was achieved for V:SM 1:0.1 nanoemulsions prepared with 0.1% Nile Red. It was confirmed that there was no release of the fluorophore neither in culture medium (<3% in DMEM supplemented with FBS, after 4 h of incubation, or in <10% after storage in a refrigerator for 4 days). After 4 h of incubation of the nanoemulsions with endometrial tumor cells (HEC1A) and colon (SW480) that would have been previously transformed to express GFP, the cells were washed and fixed with paraformaldehyde. After mounting the preparation with Mowiol (Calbiochem), they were observed under the confocal microscope (Confocal Leica Laser Microscope SP8®). As shown in FIG. 4, red fluorescence, corresponding to Nile Red-labeled nanoemulsions, was observed in cellular cytoplasms, mainly in colon cells. Similar experiments were performed with DiD labeled nanoemulsions, incubated on different types of tumor cells for 4 h (colon, lung, prostate and pancreas), and the ability of the V:SM 1:0.1 nanoemulsions to access the cellular interior was confirmed, independently of the cell line type (FIG. 4A). As for the composition of nanoemulsions, it does allow to modulate the degree of interaction. Comparing for example the cellular internalization of neutral (V:SM 1:0.1) and cationic (V:SM:DOTAP 1:0.1:0.1) nanoemulsions loaded with the 0.03% DiR fluorophore, after 4 h of incubation in colon cells HCT116, a greater intensity of fluorescence is observed in the case of positively charged nanoemulsions, probably due to the contribution of the charge for the establishment of electrostatic interactions with the cell membrane.

On the other hand, it has been confirmed that nanoemulsions are not only capable of interacting with the target cells, but also of transporting the molecules/drugs associated to the cell interior, nucleotides (GUC CAG UUU UCC CAG GAA UCC CU) (SEQ ID NO: 11) of double chain, of non-specific sequence, marked with Cy5 O:SM:Lact 1:0.1:0.1, after 4 h of incubation in colon cells.

Example 8. Interaction Studies of Functionalized Nanoemulsions with Cells Expressing Target Receptors The functionalization of the nanoemulsions with different ligands took place as described in example 3. To study the effect of functionalization in terms of the ability of nanoemulsions to interact with cells expressing the receptor of interest, techniques were used of flow cytometry and confocal microscopy.

FIG. 6 shows data from the analysis of SW620 cells analyzed by flow cytometry, to determine the number of cells showing positive fluorescence, and the intensity thereof, attributed to the nanoemulsions loaded with Nile Red that would have been internalized after 4 h incubation at 37° C. The analysis was carried out after thoroughly washing the cells with PBS, and then preparing a suspension thereof, following the usual trypsinization protocol. 100,000 cells were seeded per well in 24-well plates, and the nanosystems were added for 4 hours at 37° C. After this time, the cells were washed and trypsinized, centrifuging at 150 RCF, 5 minutes at room temperature (CentrigugaSL 16R, rotor TX-400, ThermoScientific®), to separate the cells from the medium. The supernatant was removed by aspiration, the pellet was resuspended in PBS 1×, and transferred to special cytometry tubes. After another centrifugation at 150 RCF, the supernatant was aspirated and the remaining pellet was resuspended in 0.4% paraformaldehyde in a volume of 500 μl for the attachment of the cells. The analysis was carried out in a FACScalibur team, BectonDickinson®. In FIG. 6 it is possible to observe how effectively the nanoemulsions functionalized with LAPI are internalized more efficiently with cells that overexpress the leptin receptor.

To study the internalization of nanoemulsions functionalized with lactisole, SW620 cells were used, and confocal microscopy was used. For these experiments, 80,000 cells were seeded per well in 8-well μ-chambers (PLC30108, SPL LifeSciences). After 24 hours, the cells were incubated with nanoemulsions prepared from oleic acid and a derivative of sphingomyelin labeled with NBD, which in turn encapsulated DiR (OLM; O:SM 1:0.1), and those same functionalized nanoemulsions. with lactisole (OLM-L; O:SM:Lact 1:0.1:0.1), at a final concentration in the nanoemulsion well of 0.12 mg/mL. After 4 hours of incubation at 37° C., the cells were washed with 1×PBS twice, and then fixed with 4% paraformaldehyde for 15 minutes, after which the wells were washed twice with PBS 1×, and then Cell nuclei were stained with Hoechst 33342 (Thermo Fisher®). The mounting medium (Mowiol, Calbiochem) was applied and the samples were observed under the confocal microscope (ConfocalLeica Laser Microscope SP8®). A similar experiment was carried out comparing in this case the internalization of the functionalized nanoemulsions with lactisole (O:SM:Lact 1:0.1:0.1), and labeled with DiD, after incubation in SW620 cells with cultured medium with high or low concentration of glucose, and therefore with different levels of expression of the receptor, as seen in example 6. It was found that effectively the intensity of fluorescence due to nanoemulsions decreased in the case of incubation on SW620 cells with lower expression of TAS1R3 receptor for lactisole, as can be seen in FIG. 11.

Similar results were obtained for functionalized nanoemulsions with RPM (FIG. 8). This greater internalization is related to a greater efficacy to release intracellular therapeutic molecules associated, as discussed in example 7, with respect to cell viability tests with nanoemulsions O:SM:Lact 1:0.1:0,1 (F-NE) loaded with etoposide. Similarly, FIG. 8 shows the observation of Cy5-labeled microRNA, which would have been internalized in the cell lines SW480 and SW620 after being transfected for 4 h and at 37° C. with nanoemulsions of vitamin E, sphingomyelin and oactadecylamine (V:SM:OCT 1:0.1:0.01) functionalized with RPM to which miRNA was tagged with Cy5 fluorophore (VSMSTRPMmiRNA) and control nanoemulsions (SMSTSHmiRNA). After analysis of the fluorescence by confocal microscopy, a much greater signal is seen for the nanoemulsions with RPM, which have a superior ability to release the associated therapeutic molecule at the intracellular level.

Example 9. In Vitro Therapeutic Efficacy Assays

Nanoemulsions 1:0.1:0.1 (F-NE), loaded with 1% etoposide by weight, with respect to the rest of the components, using an assay that determines cell viability, were seeded (10,000 cells per well) in a 96-well plate. After 24 h of culture, 20 μl of the test formulation was applied to 110 μl of culture medium, in increasing order of concentration, establishing as controls a positive one, adding the vehicle in which the nanosystem is dissolved (water in the largest part of the cases), and a negative one, or total death, where a dilution of Triton 100× at 6% was applied. After 48 hours, the culture medium of the plate was aspirated, washing with 1×PBS, then applying the MTT reagent at a concentration of 5 mg/mL in 1× PBS, after dilution 1:10 in DMEM medium without supplementation, and filtered with a 0.22 μm filter. 110 μl was applied per well. After 4 hours in the incubator, the medium was removed from the plate, and a volume of 110 μl of 1×DMSO (dimethylsulfoxide, 99.7%, AcrosOrganics) was added to dissolve the formazan crystals originated by the mitochondrial enzymes. Protecting the light plate was incubated 15 minutes at 37° C., to then measure the absorbance at 570 nanometers in the spectrophotometer (Multiskan EX, ThermoLabsystems®) and obtain the EC50 values of each formulation, using the GraphPad Prism 5 program. to the encapsulation of an antitumor drug, etoposide was selected, and 13.75 μl of a solution of 40 mg/mL (550 μg of drug) was added to the organic phase. All nanoemulsions were isolated by centrifugation for 30 minutes at 14000×g 15° C. (Microcentrifuge 5415R, rotor F452411 Eppendorf®), in order to eliminate everything that was not part of the nanoemulsions. As shown in FIG. 9A, greater cytotoxic activity was observed in the case of cells treated with drug nanoemulsions (whites hardly showed activity), particularly in the case of functionalized nanoemulsions.

Example 10. Therapeutic Efficacy Assays in Murine Model

To determine efficacy in murine model, biosdistribution studies by optical imaging were carried out first. Nanoemulsions O:SM 1:0.1 and O:SM:UROG 1:0.1:0.01 were labeled with DiR, adding the same to the organic phase after preparation of the nanoemulsions (0.1%). These nanoemulsions were injected intravenously into the tail vein of nude mice, females, weighing about 25-30 g, to which previously (between 6-8 weeks of age), cells on both flanks would have been inoculated SVV620 (5 million in 100 ul of an average culture mixture: matrigel 3:1, at two weeks, most tumors are palpable and have an average volume of 150 mm3). The mean volume of tumors for this experiment was 500 mm3. 24 h after the injection of the functionalized nanoemulsions (O:SM:UROG 1:0.1:0.01) and loaded with DiR, the mice were sacrificed, the organs excised, and observed by optical imaging (IVIS® imaging system). As shown in FIG. 10A, fluorescence was mainly detected in liver and tumor. In addition, a trial of therapeutic effectiveness was carried out in that same mouse model. When the tumors reached an average volume of 250 mm3, the mice were classified into two groups, one of them control, which received no treatment, and one of them that would be treated with functionalized nanoemulsions (O:SM:UROG 1:0.1:0.01) loaded with etoposide. Four injections of nanoemulsion in a total volume of 100 μL were administered intravenously in a tail vein on days 1, 4, 8 and 11 (dose 0.2 mg/kg of etoposide). The tumor volumes were monitored over time, and the relative increase in volume was represented for each evaluation time (Vt/Vo=Volume at a time/Volume at the beginning of the study). During the duration of the study, no toxic effects were observed. FIG. 10B also shows a smaller increase in tumor volume in the group of treated mice, which reveals the potential of these nanoemulsions for the development of new antitumor therapies.

The invention claimed is:

1. An oil in water (o/w) nanoemulsion, comprising:

a) an aqueous phase;

b) an oily nucleus comprising vitamin E; and c) sphingomyelin, wherein a mass ratio (w/w) of the vitamin E to the sphingomyelin ranges from 1:0.01 to 1:10.

2. The nanoemulsion according to claim 1, wherein the nanoemulsion is functionalized with at least one of:

d) one or more therapeutic molecule; and e) one or more contrast agent.

3. The nanoemulsion according to claim 2, wherein the nanoemulsion is functionalized with one or more therapeutic molecule selected from the group consisting of an antitumor drug, an anti-inflammatory drug, an anti-angiogenic drug, a nucleic acid, a biomolecule, and any combination thereof.

4. The nanoemulsion according to claim 2, wherein the nanoemulsion is functionalized with one or more contrast element selected from the list consisting of a fluorophore, a superparamagnetic iron oxide nanoparticle (SPION) or derivatives thereof, a radioisotope, a perfluorohexane, an octafluoropropane, and any combination thereof.

5. The nanoemulsion according to claim 1, wherein the nanoemulsion is functionalized with at least one ligand capable of interacting or binding to receptors expressed on a cell membrane.

6. The nanoemulsion according to claim 5, wherein the at least one ligand is capable of binding to the TAS1R3 receptor.

7. The nanoemulsion according to claim 6, wherein the at least one ligand is a brazzein-derived peptide, a lactisole sweetener, or a combination thereof.

8. The nanoemulsion according to claim 5, wherein the nanoemulsion is functionalized with at least one ligand capable of interacting or binding to leptin receptor, guanylyl cyclase, uroguaniline, uroguaniline modified with lysines, extracellular fraction of an integrin, or SEQ ID NO:4.

9. The nanoemulsion according to claim 1, further comprising at least one selected from the group consisting of a phospholipid, a sterol, a glycolipid, N-[1-(2,3-Dioleoyloxy)propyl]-N,N,N-trimethylammonium methyl-sulfate (DOTAP), octadecylamine, a polyamine, a polyethylene glycol (PEG), a surfactant, a coating polymer, and any combination thereof, arranged in an interface of the nanoemulsion.

10. The nanoemulsion according to claim 2, wherein the nanoemulsion is functionalized with at least one ligand capable of interacting or binding to receptors expressed on a cell membrane.

11. The nanoemulsion according to claim 3, wherein the nanoemulsion is functionalized with at least one ligand capable of interacting or binding to receptors expressed on a cell membrane.

12. The nanoemulsion according to claim 4, wherein the nanoemulsion is functionalized with at least one ligand capable of interacting or binding to receptors expressed on a cell membrane.

13. The nanoemulsion, according to claim 1, wherein the vitamin E is α-tocopherol.

14. The nanoemulsion according to claim 2, wherein the nanoemulsion is functionalized with one more therapeutic molecule selected from the group consisting of carmofur, etoposide docetaxel, 5-fluorouracil, paclitaxel, gemcitabine, edelfosine, curcumin, verteporfin, resveratrol, a pDNA, a shRNA, a miRNA, a mRNA, a peptide, an antibody, an aptamer, and any combination thereof.

15. The nanoemulsion according to claim 1, wherein the oily nucleus consists of the vitamin E.

16. The nanoemulsion according to claim 1, wherein a concentration (w/v) of the sphingomyelin ranges from 1% to 6% by weight based on a total volume of the nanoemulsion.

17. The nanoemulsion according to claim 1, wherein the mass ratio (w/w) of the vitamin E to the sphingomyelin ranges from 1:0.01 to 1:1.

* * * * *

SEQUENCE LISTING

```
Sequence total quantity: 11
SEQ ID NO: 1            moltype = AA  length = 16
FEATURE                 Location/Qualifiers
MOD_RES                 1..16
                        note = C18-PEG12
source                  1..16
                        mol_type = protein
                        note = UROG
```

-continued

```
                          organism = synthetic construct
SEQUENCE: 1
NDDCELCVNV ACTGCL                                                     16

SEQ ID NO: 2              moltype = AA  length = 22
FEATURE                   Location/Qualifiers
DISULFID                  10..18
                          note = Disulfide between C in position 10 and 18
DISULFID                  13..21
                          note = disulfide bond between Cys in position 13 and 21
source                    1..22
                          mol_type = protein
                          note = UROGLys
                          organism = synthetic construct
SEQUENCE: 2
KKKKKKNDDC ELCVNVACTG CL                                              22

SEQ ID NO: 3              moltype = AA  length = 7
FEATURE                   Location/Qualifiers
source                    1..7
                          mol_type = protein
                          note = BRA
                          organism = synthetic construct
SEQUENCE: 3
CFYDEKR                                                               7

SEQ ID NO: 4              moltype = AA  length = 9
FEATURE                   Location/Qualifiers
MOD_RES                   1
                          note = C18-PEG
source                    1..9
                          mol_type = protein
                          note = RPM
                          organism = synthetic construct
SEQUENCE: 4
CPIEDRPMC                                                             9

SEQ ID NO: 5              moltype = AA  length = 9
FEATURE                   Location/Qualifiers
source                    1..9
                          mol_type = protein
                          note = RPM peptide
                          organism = synthetic construct
SEQUENCE: 5
CPIEDRPMC                                                             9

SEQ ID NO: 6              moltype = AA  length = 8
FEATURE                   Location/Qualifiers
source                    1..8
                          mol_type = protein
                          note = RPM
                          organism = synthetic construct
SEQUENCE: 6
VSMSTRPM                                                              8

SEQ ID NO: 7              moltype = AA  length = 7
FEATURE                   Location/Qualifiers
source                    1..7
                          mol_type = protein
                          note = Control
                          organism = synthetic construct
SEQUENCE: 7
VSMSTSH                                                               7

SEQ ID NO: 8              moltype = AA  length = 8
FEATURE                   Location/Qualifiers
MOD_RES                   8
                          note = miRNA
source                    1..8
                          mol_type = protein
                          note = RPM-miRNA
                          organism = synthetic construct
SEQUENCE: 8
VSMSTRPM                                                              8

SEQ ID NO: 9              moltype = AA  length = 7
FEATURE                   Location/Qualifiers
MOD_RES                   7
                          note = miRNA
```

-continued

```
source                1..7
                      mol_type = protein
                      note = Control-miRNA
                      organism = synthetic construct
SEQUENCE: 9
VSMSTSH                                                             7

SEQ ID NO: 10         moltype = AA  length = 5
FEATURE               Location/Qualifiers
MOD_RES               1
                      note = C18-PEG8
source                1..5
                      mol_type = protein
                      note = LAPI
                      organism = synthetic construct
SEQUENCE: 10
LDFIK                                                               5

SEQ ID NO: 11         moltype = RNA  length = 23
FEATURE               Location/Qualifiers
misc_feature          1..23
                      note = sythetic nucleotide
source                1..23
                      mol_type = other RNA
                      organism = synthetic construct
SEQUENCE: 11
gtccagtttt cccaggaatc cct                                           23
```